US012735723B2

(12) United States Patent
Rodino-Klapac et al.

(10) Patent No.: US 12,735,723 B2
(45) Date of Patent: Sep. 15, 2026

(54) SELF-COMPLEMENTARY ADENO-ASSOCIATED VIRUS VECTOR AND ITS USE IN TREATMENT OF MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, Columbus, OH (US); Jerry R. Mendell, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 830 days.

(21) Appl. No.: 18/060,263

(22) Filed: Nov. 30, 2022

(65) Prior Publication Data

US 2023/0279431 A1 Sep. 7, 2023

Related U.S. Application Data

(60) Provisional application No. 63/284,418, filed on Nov. 30, 2021.

(51) Int. Cl.

*C12N 15/86* (2006.01)
*A61K 48/00* (2006.01)
*C07K 14/47* (2006.01)

(52) U.S. Cl.

CPC .......... *C12N 15/86* (2013.01); *A61K 48/0058* (2013.01); *C07K 14/4707* (2013.01); *C12N 2750/14143* (2013.01); *C12N 2840/007* (2013.01)

(58) Field of Classification Search

None

See application file for complete search history.

(56) References Cited

U.S. PATENT DOCUMENTS 5,173,414 A 12/1992 Lebkowski et al.
5,449,616 A * 9/1995 Campbell ............ C07K 14/705 435/325
5,658,776 A 8/1997 Flotte et al.
5,672,694 A 9/1997 Campbell et al.
5,786,211 A 7/1998 Johnson (Continued)

FOREIGN PATENT DOCUMENTS

CN 101896186 A 11/2010
EP 0 127 839 A2 12/1984

(Continued)

OTHER PUBLICATIONS

Anderson et al., Nucleic Acid Hybridisation: a Practical Approach, IRL Press Limited, Oxford, England, Ch. 4.

(Continued)

*Primary Examiner* — Tracy Vivlemore
*Assistant Examiner* — Hanna Marie Thueson
(74) *Attorney, Agent, or Firm* — Foley & Lardner LLP

(57) ABSTRACT

Described herein are methods of treating muscular dystrophy comprising administering a self complementary recombinant AAV (rAAV) scAAVrh74.tMCK.hSGCA vector, methods of expressing alpha-sarcoglycan gene in a patient, pharmaceutical compositions comprising the rAAV, and methods of generating the rAAV.

18 Claims, 5 Drawing Sheets

Specification includes a Sequence Listing.

scAAVrh.74.tMCK.hSGCA

ITR=Inverted Terminal Repeat, hSGCA=Human Alpha-Sarcoglycan, pA=Polyadenylation Sequence, AAV=Adeno-Associated Virus

(56) References Cited

U.S. PATENT DOCUMENTS 5,871,982 A 2/1999 Wilson et al.
6,204,059 B1 3/2001 Samulski et al.
6,258,595 B1 7/2001 Gao et al.
6,262,035 B1 7/2001 Campbell et al.
6,566,118 B1 5/2003 Atkinson et al.
6,632,800 B1 10/2003 Russell et al.
7,282,199 B2 10/2007 Gao et al.
7,759,314 B2 7/2010 Fallon et al.
7,790,449 B2 9/2010 Gao et al.
7,883,858 B2 2/2011 Hood et al.
9,061,059 B2 6/2015 Chakraborty et al.
9,434,928 B2 9/2016 Mendell et al.
10,105,453 B2 10/2018 Mendell et al.
11,358,993 B2 6/2022 Rodino-Klapac et al.
11,845,952 B2 12/2023 Okada et al.
2001/0029040 A1 10/2001 Toyo-Oka
2003/0225260 A1 12/2003 Snyder
2006/0154250 A1 7/2006 Morris et al.
2007/0099251 A1 5/2007 Zhang et al.
2008/0249052 A1 10/2008 Duan et al.
2009/0054823 A1 2/2009 Bridges et al.
2009/0275107 A1 11/2009 Lock et al.
2009/0280103 A1 11/2009 Flueck
2010/0003218 A1 1/2010 Duan et al.
2010/0008979 A1 1/2010 Tomatsu et al.
2010/0026655 A1 2/2010 Harley
2010/0075866 A1 3/2010 Hood et al.
2010/0112694 A1 5/2010 Marban
2010/0120627 A1 5/2010 Belouchi et al.
2010/0247495 A1 9/2010 Ichim et al.
2010/0266551 A1 10/2010 Richard et al.
2011/0023139 A1 1/2011 Weinstein et al.
2011/0053221 A1 3/2011 Chen et al.
2011/0070210 A1 3/2011 Andrijauskas
2011/0076744 A1 3/2011 Wright et al.
2011/0082192 A1 4/2011 Milne et al.
2011/0104120 A1 5/2011 Xiao et al.
2011/0266551 A1 11/2011 Thompson et al.
2011/0294193 A1 12/2011 Amalfitano et al.
2011/0301226 A1 12/2011 Mendell et al.
2012/0087862 A1 4/2012 Hood et al.
2013/0171172 A1 7/2013 Richard et al.
2014/0010861 A1 1/2014 Bancel et al.
2014/0147432 A1 5/2014 Chakraborty et al.
2014/0179770 A1 6/2014 Zhang et al.
2014/0234255 A1 8/2014 Lai et al.
2014/0249208 A1 9/2014 Chakraborty et al.
2014/0256802 A1 9/2014 Boye et al.
2014/0273231 A1 9/2014 Zhang et al.
2014/0323956 A1 10/2014 Mendell et al.
2015/0111955 A1 4/2015 High et al.
2015/0125429 A1 5/2015 Perlingeiro et al.
2015/0232883 A1 8/2015 Dahlman et al.
2015/0238627 A1 8/2015 Leger et al.
2016/0058890 A1 3/2016 Buj Bello et al.
2016/0272976 A1 9/2016 Kaspar et al.
2018/0256752 A1 9/2018 Buj Bello et al.
2019/0000998 A1 1/2019 Mendell et al.
2019/0202880 A1 7/2019 Rodino-Klapac et al.
2019/0343966 A1 11/2019 Wang et al.
2020/0339960 A1* 10/2020 Sahenk .................. A61P 25/00
2021/0128749 A1 5/2021 Rodino-Klapac et al.
2021/0393801 A1 12/2021 Rodino-Klapac et al.
2023/0390417 A1 12/2023 Sahenk

FOREIGN PATENT DOCUMENTS

EP 0 155 476 A 9/1985
EP 2 859 896 A1 4/2015
JP 2006-121961 A 5/2006
JP 2015/509711 A 4/2015
WO 95/03392 A1 2/1995
WO 95/13365 A1 5/1995
WO 95/13392 A1 5/1995
WO 96/17947 A1 6/1996
WO 97/06243 A1 2/1997
WO 97/08298 A1 3/1997
WO 97/09441 A2 3/1997
WO 97/21825 A1 6/1997
WO 98/09657 A2 3/1998
WO 99/01176 A1 1/1999
WO 99/11764 A2 3/1999
WO WO-99/43360 A1 9/1999
WO 01/83692 A2 11/2001
WO 02/53703 A2 7/2002
WO WO-03/074714 A1 9/2003
WO 2004/058146 A2 7/2004
WO WO-2007/057781 A2 5/2007
WO WO-2009/019505 A2 2/2009
WO 2009/054725 A2 4/2009
WO 2013/016352 A1 1/2013
WO 2013/078316 A1 5/2013
WO WO-2013/123503 A1 8/2013
WO WO-2013/151665 A2 10/2013
WO WO-2013/176772 A1 11/2013
WO WO-2014/037526 A1 3/2014
WO WO-2014/039916 A1 3/2014
WO WO-2014/093622 A2 6/2014
WO WO-2014/093712 A1 6/2014
WO WO-2014/204725 A1 12/2014
WO WO-2015/018503 A1 2/2015
WO WO-2015/021457 A2 2/2015
WO 2015/110449 A1 7/2015
WO WO-2015/158749 A2 10/2015
WO 2015/197232 A1 12/2015
WO WO-2016/115543 A2 7/2016
WO WO-2017/087395 A1 5/2017
WO WO-2017/165859 A1 9/2017
WO 2017/180857 A1 10/2017
WO 2017/180976 A1 10/2017
WO WO-2017/181014 A1 10/2017
WO WO-2017/181015 A1 10/2017
WO WO-2017/221145 A1 12/2017
WO WO-2018/170408 A1 9/2018
WO WO-2019/012336 A1 1/2019
WO WO-2019/078916 A1 4/2019
WO WO-2019/118806 A1 6/2019
WO WO-2019/152474 A1 8/2019
WO WO-2019/155833 A1 8/2019
WO WO-2019/195362 A1 10/2019
WO WO-2019/209777 A1 10/2019
WO WO-2019/245973 A1 12/2019
WO WO-2020/006458 A1 1/2020
WO WO-2020/123645 A1 6/2020
WO WO-2020/176614 A1 9/2020
WO WO-2020/210595 A1 10/2020
WO WO-2021/035120 A1 2/2021
WO WO-2021/126880 A1 6/2021
WO WO-2021/257655 A1 12/2021
WO WO-2022/055791 A2 3/2022

OTHER PUBLICATIONS

Angelini et al., The clinical spectrum of sarcoglycanopathies, Neurology, 52(1):176-179 (1999).

Araishi et al., Loss of the sarcoglycan complex and sarcospan leads to muscular dystrophy in beta-sarcoglycan-deficient mice, Hum. Mol. Genet., 8(9):1589-1598 (1999).

Barresi et al., Disruption of heart sarcoglycan complex and severe cardiomyopathy caused by beta sarcoglycan mutations, J. Med. Genet., 37(2):102-107 (2000).

Beastrom et al., mdx(5cv) mice manifest more severe muscle dysfunction and diaphragm force deficits than do mdx Mice, Am. J. Pathol., 179(5):2464-74 (2011).

Bonnemann et al., Betasarcoglycan (A3b) mutations cause autosomal recessive muscular dystrophy with loss of the sarcoglycan complex, Nat. Genet., 11(3):266-273 (1995).

Bonnemann et al., Genomic screening for beta-sarcoglycan gene mutations: missense mutations may cause severe limb-girdle muscular dystrophy type 2E (LGMD 2E), Hum. Mol. Genet., 5(12):1953-1961 (1996).

Carter, Adeno-associated virus vectors, Current Opinions in Biotechnology, 3(5):533-539 (1992).

(56) References Cited

OTHER PUBLICATIONS

Chao et al., Several log increase in therapeutic transgene delivery by distinct adeno-associated viral serotype vectors, Mol. Ther., 2(6):619-623 (2000).
Chao et al., Sustained and complete phenotype correction of hemophilia B mice following intramuscular injection of AAV1 serotype vectors, Mol. Ther., 4(3):217-222 (2001).
Chicoine et al., Plasmapheresis eliminates the negative impact of AAV antibodies on microdystrophin gene expression following vascular delivery, Mol. Ther., 22(2):338-347 (2014).
Chicoine et al., Vascular delivery of rAAVrh74.MCK.GALGT2 to the gastrocnemius muscle of the rhesus macaque stimulates the expression of dystrophin and laminin a2 surrogates, Mol. Ther., 22(4):713-724 (2014).
Clark et al., A stable cell line carrying adenovirus-inducible rep and cap genes allows for infectivity titration of adeno-associated virus vectors, Gene. Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
Clark et al., Recombinant adeno-associated viral vectors mediate long-term transgene expression in muscle, Hum. Gene. Ther., 8(6):659-669 (1997).
Cserjesi et al., Myogenin induces the myocyte-specific enhancer binding factor MEF-2 independently of other muscle-specific gene products, Mol. Cell. Biol., 11(10):4854-4862 (1991).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Draviam et al., The -li-core of sarcoglycan is essential for deposition at the plasma membrane, Muscle and Nerve. 34:691-701 (2006).
Dressman et al., Delivery of alpha- and beta-sarcoglycan by recombinant adeno-associated virus: efficient rescue of muscle, but differential toxicity, Hum. Gene. Ther., 13(13):1631-1646 (2002).
Dressman, D., AAV-Mediated gene transfer to models of muscular dystrophy: Insights into assembly of multi-subunit membrane proteins, University of Pittsburgh (1997).
Durbeej et al., Disruption of the beta-sarcoglycan gene reveals pathogenetic complexity of limb-girdle muscular dystrophy type 2E, Mol. Cell., 5(1):141-151 (2000).
Fanin et al., LGMD2E patients risk developing dilated cardiomyopathy, Neuromuscl. Disord., 13(4):303-309 (2003).
Flotte et al., Gene expression from adeno-associated virus vectors in airway epithelial cells, Am. J. Respir Mol. Biol. 7:349-356. 1992.
Gao et al., Clades of Adeno-associated Viruses Are Widely Disseminated in Human Tissues, J. Virol., 78:6381-6388 (2004).
GenBank Accession No. AF085716.1, Adena-associated virus 5 DNA binding trs helicase (Rep22) and capsid protein (VP1) aenes, complete eds, Feb. 9, 1999.
GenBank Accession No. AX753246.1, Sequence 1 from Patent EP1310571, Jun. 23, 2003.
GenBank Accession No. AX753249.1, Sequence 4 from Patent EP1310571, Jun. 23, 2003.
Genbank Accession No. NC_001401.0, Adena-associated virus—2, complete genome, Aug. 13, 2018.
Genbank Accession No. NC_001729.1, Adena-associated virus—3, complete genome, Aug. 13, 2018.
GenBank Accession No. NC_001829.1, Adena-associated virus—4, complete genome, Aug. 13, 2018.
GenBank Accession No. NC_001862, Adena-associated virus 6, complete genome, Jan. 12, 2004.
Genbank Accession No. NC_002077.1, Adena-associated virus—1, complete genome, Aug. 13, 2018.
Genbank Accession No. NM_00232.4, *Homo sapiens* sarcoglycan beta (SGCB), Mrna, Feb. 20, 2019.
Genbank Accession No. NP_000233.1, Beta Sarcoglyan (43kD dystrophin-associated glycoprotein) *Homo Sapiens*, Mar. 19, 1999.
GenBank: Accession No. NP_000223.1: beta-sarcoglycan sequence, dated Mar. 3, 1999.
Gibertini et al., Fibrosis and inflammation are greater in muscles of beta-sarcoglycan-null mouse than mdx mouse, Cell Tissue Res., 356(2):427-443 (2014).
Greig et al., Impact of intravenous infusion time on AAV8 vector pharmacokinetics, safety, and liver transduction in cynomolgus macaques, Mol. Ther. Methods Clin. Dev., 3(C):16079 (2016).
Grieger et al., Production and characterization of adeno-associated viral vectors, Nat. Protoc., 1(3):1412-1428 (2006).
Hakim et al., The passive mechanical properties of the extensor digitorum longus muscle are compromised in 2- to 20-mo-old mdx mice, J. Appl. Physiol., 110(6):1656-1663 (2011).
Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).
Herzog et al., Stable gene transfer and expression of human blood coagulation factor IX after intramuscular injection of recombinant adeno-associated virus, Proc. Natl. Acad. Sci. USA, 94(11):5804-5809 (1997).
International Application No. PCT/US2017/027583, International Preliminary Report on Patentability, mailed Oct. 25, 2018.
International Application No. PCT/US2017/027583, International Search Report and Written Opinion, mailed Jul. 14, 2017.
International Application No. PCT/US2020/019892, International Preliminary Report on Patentability, mailed Sep. 10, 2021.
International Application No. PCT/US2020/019892, International Search Report and Written Opinion, mailed May 14, 2020.
International Preliminary Report on Patentability, PCT/US2017/027636 (Oct. 16, 2018).
International Search Report and Written Opinion, PCT/US2017/027636 (Jul. 5, 2017).
Johnson et al., Muscle creatine kinase sequence elements regulating skeletal and cardiac muscle expression in transgenic mice, Mol. Cell. Biol., 9(8):3393-3399 (1989).
Kessler et al., Gene delivery to skeletal muscle results in sustained expression and systemic delivery of a therapeutic protein, Proc. Nat. Acad. Sci. USA, 93(24):14082-14087 (1996).
Kobayashi et al., Sarcolemma-localized nNOS is required to maintain activity after mild exercise, Nature. 456:511-5 (2008).
Chu et al., "The limb-girdle muscular dystrophies: is treatment on the horizon?" Neurotherapeutics, 15(4):849-862 (Oct. 2018).
Monies et al., "A first-line diagnostic assay for limb-girdle muscular dystropy and other nyopathies", Human Genomics, 10(1):32, pp. 1-7 (Sep. 27, 2016).
Theadom et al., "Prealence of muscular dystrophies: a systematic literature review," Neuroepidemiology 43(3-4):259-68 (2014).
Thomas et al., "B4GALNT2 (GALGT2) Gene Therapy Reduces Skeletal Muscle Pathology in the FKRP P448L Mouse Model of Limb Girdle Muscular Dystrophy 21", Am. J_ Pathol., 186(9):2429-2448 (2016).
Wagner et al., "A novel method for the quantification of adeno-associated virus vectors for RNA interference applications using quantitative polymerase chain reaction and purified genomic adeno-associated virus DNA as a standard," Human Gene Therapy Methods, 24(6):355-63 (Dec. 2013).
Walter et al., "Recent developments in Duchenne muscular dystrophy: facts and numbers," Journal of Cachexia, Sarcopenia and Muscle, 8(5):681-685 (Oct. 2017).
Werling et al., "Systematic comparison and validation of quantitative real-time PCR methods for the quantitation of adeno-associated viral products," Human Gene Therapy Methods, 26.3:82-92 (Jun. 2015).
Griffin et al. Preclinical systemic delivery of adeno-associated [alpha]-sarcoglycan gene transfer for limb-girdle mscular dystrophy, Human Gene Therapy, 32(7-8): 390-404, (Apr. 2021).
Raj Deepak et al., Self-complementary adeno-associated viral vectors for gene therapy of a hemophilia B: progress and challenges, Exert Review of Hemtol. England, Informa Uk, 4(5): 539-549, (Nov. 2011).
Mendell et al., Sustained alpha-sarcoglycan gene expression after gene transfer in linb-girdle muscular dystrophy, tye 2D, Annals of Neurol. 68(5): 629-638, (Oct. 2010).

(56) References Cited

OTHER PUBLICATIONS

Inouye et al., Codon optimization of genes for efficient protein expression in mammalian cells by selection of only preferred human codons, Protein Expression and Purification, 109: 47-54, (May 2015).
Srivastava et al., Nucleotide Sequence and Organization of the Adeno-Associated Virus 2 Genome, J. Virol., 45:555-564 (1983).
Straub et al., Animal models for muscular dystrophy show different patterns of sarcolemmal disruption, J. Cell. Biol., 139(2):375-385 (1997).
Sun et al., Correction of Multiple Striated Muscles in Murine Pompe Disease Through Adena-Associated Virus-mediated Gene Therapy, Mol. Ther., 16(8):1366-71 (2008).
Sveen et al., Cardiac involvement in patients with limb-girdle muscular dystrophy type 2 and Becker muscular dystrophy, Arch. Neurol., 65(9):1196-1201 (2008).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
Voikar et al., Long-term individual housing in C57BL/6J and DBA/2 mice: assessment of behavioral consequences, Genes Brain Behav., 4(4):240-52 (2005).
Wang et al., Construction and analysis of compact muscle-specific promoters for AAV vectors, Gene. Ther., 15(22):1489-1499 (2008).
Wang et al., Loss of miR-29 in myoblasts contributes to dystrophic muscle pathogenesis, Mol. Ther., 20(6):1222-33 (2012).
Wein et al., Translation from a DMD exon 5 IRES results in a functional dystrophin isoform that attenuates dystrophinopathy in humans and mice, Nat. Med., 20(9):992-1000 (2014).
Weintraub et al., The myoD gene family: nodal point during specification of the muscle cell lineage, Science. 251:761-766 (1991).
Wong-Kisiel et al., Two siblings with limb-girdle muscular dystrophy type 2E responsive to deflazacort, Neuromusc. Disord., 20(2):122-124 (2010).
Xiao et al., Efficient long-term gene transfer into muscle tissue of immunocompetent mice by adeno-associated virus vector, J. Virol., 70(11):8098-8108 (1996).
Xiao et al., Production of High-Titer Recombinant Adeno-Associated Virus Vectors in the Absence of Helper Adenovirus, J. Virol., 72:2224-2232 (1998).
Xu et al., An Isolated Limb Infusion Method Allows for Broad Distribution of rAAVrh74.MCK.GALGT2 to Leg Skeletal Muscles in the Rhesus Macaque, Mol. Ther. Methods Clin. Dev., 10:89-104 (2018).
Zanotti et al., Opposing roles of miR-21 and miR-29 in the progression of fibrosis in Duchenne muscular dystrophy., Biochem. Biophys. Acta., 1852:1451-4 (2015).
Zhang et al., Dual AAV therapy ameliorates exercise-induced muscle injury and functional ischemia in murine models of Duchenne muscular dystrophy, Hum. Mol. Genet. 22:3720-9 (2013).
Dorange et al., "Analytical approaches to characterize AAV vector production & purification: Advances and challenges," Cell & Gene Therapy Insights, 4(2):119-129 (2018).
Hou et al., "Serious Overestimation in Quantitative PCR by Circular (Supercoiled) Plasmid Standard: Microalgal pcna as the Model Gene," PLoS One 5(3):e9545, 8 pages (Mar. 5, 2010) doi:10.1371/journal.pone.0009545.
Martinez-Fernandez de la Camara et al., "The accurate quantification of AAV genomic titre depends on the conformation of the plasmid reference," ARVO Annual Meeting Abstract, 3 pages, Jul. 2018.
Wu et al., "Adeno-associated virus serotypes: vector toolkit for human gene therapy." Molecular therapy 14.3 (2006): 316-327 (Year: 2006).
Abadi et al., Supplementation with alpha-lipoic acid, CoQ10, and vitamin E augments running performance and mitochondrial function in female mice, PLoS One, 8(4):e60722 (2013).
ABSS (Sequence Alignment; WO2020006458, Seq Id #1; accessed Mar. 12, 2024) (Year: 2024).
ABSS2 (Sequence Alignment; U.S. Appl. No. 17/255,488, Seq Id #1; accessed Mar. 12, 2024) (Year: 2024).
Allamand et al., Early adenovirus-mediated gene transfer effectively prevents muscular dystrophy in alpha-sarcoglycan-deficient mice, Gene Ther., 7(16):1385-91 (2000).
Anderson et al., "Quantitative Filter Hybridisation—Chapter 4", Nucleic acid hyridisation a practical approach, 1985, pp. 73-111.
Arnold et al., Electrophysiological Biomarkers in Spinal Muscular Atrophy: Preclinical Proof of Concept, Ann. Clin. Transl. Neural., 1 (1 ):34-44 (Jan. 2014).
Asokan et al., The AAV Vector Toolkit: Poised at the Clinical Crossroads; Molecular Therapy, 20(4):699-708 (2012).
Au et al., "Gene therapy advances: a meta-analysis of AAV Usage in Clinical Settings," Frontiers in Medicine, Feb. 9, 2022, vol. 8 (pp. 1-14).
Bang et al., The complete gene sequence of titin, expression of an unusual approximately 700-kDa titin isoform, and its interaction with obscurin identify a novel Z-line to I-band linking system, Gire. Res. 89:1065-72 (2001).
Bartoli et al., "Safety and efficacy of AA V-mediated calpain 3 gene transfer in a mouse model of limb-girdle muscular dystrophy type 2A", Mol. Ther., 13(2):250-259 (2006).
Bearzi et al., Human cardiac stem cells, Proc. Natl. Acad. Sci. USA. 104:14068-73 (2007).
Behlke, Chemical modification of siRNAs for in vivo use, Oligonucleotides. 18:305-319 (2008).
Belfort et al., Homing endonucleases: from genetic anomalies to programmable genomic clippers Methods Mal. Biol. 1123:1-26 (2014).
Boch et al., Breaking the code of DNA binding specificity of TAL-type III effectors, Science. 326:1509-12 (2009).
Boissel et al., "megaTALs" a rare-cleaving nuclease architecture for therapeutic genome engineering, Nucleic Acids Research, 2014, vol. 42, No. 4 (pp. 2591-2601).
Boissel et al., Assembly and characterization of megaTALs for hyperspecific genome engineering applications, Methods Mal. Biol. 1239:171-96 (2015).
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, 86, Feb. 12, 2010, (pp. 213-221).
Bouquet et al., Miyoshi-like distal myopathy with mutations in anoctamin 5 gene, Rev. Neural. (Paris), 168(2):135-41 (Feb. 2012).
Bramsen et al., Development of therapeutic-grade small interfering RNAs by chemical engineering, Front. Genet. 20:154 (2012).
Ceccadi et al., Homologous recombination-deficient tumors are hyper-dependent on POLQ mediated repair, Nature. 518:258-262 (2015).
Cekaite et al., "Gene expression analysis in blood cells in response to unmodified and 2'-modified siRNAs reveals TLR-dependent and independent effects," Journal of Molecular Biology, 2007, vol. 365 (pp. 90-108).
Centner et al., Identification of muscle specific ring finger proteins as potential regulators of the titin kinase domain, J. Mal. Biol. 306:717-26 (2001).
Cermak et al., "Efficient design and assembly of custom TALEN and other TAL effector-based constructs for DNA targeting," Nucleic Acids Research, 2011, (pp. 1-11).
Cermak et al., Efficient design and assembly of custom TALENs using the Golden Gate platform, Methods Mal. Biol. 1239:133-59 (2015).
Ceyhan-Birsoy et al., Recessive truncating titin gene, TTN, mutations presenting as centronuclea1 myopathy, Neuroloov. 81:1205-14 (2013).
Chandrasekharan et al., Genetic defects in muscular dystrophy, Methods Enzymol. 479:291-322 (2010).
Chauveau et al., A rising titan: TTN review and mutation update, Human Mutation. 35:1046-59 (2014).

(56) References Cited

OTHER PUBLICATIONS

Chernolovskaya et al., Chemical modification of siRNA, Curr. Opin. Mal. Ther. 12:158-67 (2010).
Chiorini et al., Cloning and characterization of adeno-associated virus type 5, J. Viral., 73(2):1309-19 (Feb. 1999).
Chiorini et al., Cloning of adeno-associated virus type 4 (AAV4) and generation of recombinant AAV4 particles, J. Viral., 71 (9):6823-33 (Sep. 1997).
Cho et al., DNA repair: Familiar ends with alternative endings, Nature. 518:174-6 (2015).
Chu et al., "SV40 DNA transfection of cells in suspension: analysis of the efficiency of transcription and translation of T-antigen", GENE, 13, (1981) 197-202.
Cordier et al., "Muscle-Specific Promoters May Be Necessary for Adeno-Associated Virus-Mediated Gene Transfer in the Treatment of Muscular Dystrophies," Human Gene Therapy, Jan. 20, 2001, vol. 12, pp. 205-215.
Cordier et al., "Rescue of Skeletal Muscles of gamma-Sarcoglycan-Deficient Mice with Adeno-Associated Virus-Mediated Gene Transfer," Molecular Therapy, Feb. 2000, vol. 1, No. 2 pp. 119-129.
Cox et al., "Therapeutic genome editing: prospects and challenges," Nature Medicine, Feb. 21, 2015, vol. 2 (pp. 121-131).
D'Amario et al., Functionally competent cardiac stem cells can be isolated from endomyocardial biopsies of patients with advanced cardiomyopathies, Gire. Res. 108:857-61 (2011).
Database Genbank [online], Accession No. AJ277892.2, Nov. 14, 2006 issue.
Daya et al., "Gene Therapy Using Adeno-Associated Virus Vectors," Clinical Microbiology Reviews, Oct. 2008, vol. 21, No. 4 (pp. 583-593).
Deleavey et al., Chemical modification of siRNA, Curr. Protoc. Nucleic Acid Chem. Chapter 16:Unit 16.3 (2009).
Doench et al., "Optimized sgRNA design to maximize activity and minimize off-target effects of CRISPR-Cas9," Nature Biotechnology, Feb. 2016, vol. 34, No. 2 (pp. 184-191).
Dreier et al., "Development of Zinc Finger Domains for Recognition of the 5'-ANN-3' Family of DNA Sequences and Their Use in the Construction of Artificial Transcription Factors," The Journal of Biological Chemistry, Aug. 3, 2001, vol. 276, No. 31 (pp. 29466-29478).
Dreier et al., Insights into the molecular recognition of the 5'-GNN-3' family of DNA sequences by zinc finger domains, J. Mal. Biol. 303:489-502 (2000).
Dreier, B. et al., "Development of zinc finger domains for recognition of the 5'-CNN-3' family DNA sequence and their use in the construction of artificial transcription factors", The Journal of Biological Chemistry, vol. 280, No. 42, Oct. 21, 2005, pp. 35588-3597.
Fanin et al., Gender difference in limb-girdle muscular dystrophy: a muscle fiber morphometric study in 101 patients, Clin. Neuropathology, 33:179-801 (2014).
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Forbes et al., "Skeletal muscles of ambulant children with Duchenne muscular dystrophy: validation of multicenter study of evaluation with MR imaging and MR spectroscopy", Radiology, 269:198-207 (2013).
Fowler, et al., Improved knockdown from artificial microRNAs in an enhanced miR-155 Backbone: a designer's guide to potent multi-target RNAi, Nucleic Acids Research, 44(5): e48, (Nov. 2015).
Foye, Whole Genome Sequencing Solved Our Family's Genetic Mystery: Titin, Narrat. Inq. Bioeth 5:206-8 (2015).
Francois, et al., Accurate Titration of Infectious AAV Particles Requires Measurement of Biologically Active Vector Genomes and Suitable Controls. Molecular Therapy—Methods & Clinical Development, Sep. 21, 2018, vol. 10, pp. 223-236.
Fucini et al., Adenosine modification may be preferred for reducing siRNA immune stimulation, Nucleic Acid Ther. 22:205-210 (2012).
Gaglione et al., Recent progress in chemically modified siRNAs, Mini. Rev. Med. Chem. 10:578-9t (2010).
Gao et al., A novel and efficient model of coronary artery ligation and myocardial infarction in the mouse, Gire. Res. 107:1445-53 (2010).
Gao et al., A novel and efficient model of coronary artery ligation in the mouse, Methods Mal. Bic 1037:299-311 (2013).
Gao et al., Adeno-associated viruses undergo substantial evolution in primates during natural infections, Proc. Natl. Acad. Sci. U.S.A., 2003, vol. 100, pp. 6081-6086.
Gautel et al., The central Z-disk region of titin is assembled from a novel repeat in variable copy numbers, Journal of Cell Science. 109:2747-2754 (1996).
Gebeyehu, et al., "Novel biotinylated nucleotide—analogs for labeling and colorimetric detection of DNA," Nucleic Acids Research, vol. 15, No. 11, (Jun. 11, 1987), p. 4513-4534.
GenBank Accession No. AF028704.1, Adena-associated virus 6, complete genome, Jan. 12, 1998.
GenBank Accession No. AF028705.1, Adeno-associated virus 3B, complete genome, Jan. 12, 1998.
GenBank Accession No. AX753250.1, Sequence 5 from Patent EP1310571, Jun. 23, 2003.
GenBank Accession No. AY631965.1, Adena-associated virus 10 nonstructural protein and caps protein genes, complete eds, Nov. 30, 2004.
GenBank Accession No. AY631966.1, Adena-associated virus 11 nonstructural protein and caps protein genes, complete eds, Nov. 30, 2004.
GenBank Accession No. DO813647.1, Adena-associated virus 12 Rep78 and VP1 genes, complete eds, Feb. 20, 2008.
GenBank Accession No. EU285562.1, Adena-associated virus 13 nonstructural protein and capsid protein genes, complete eds, Sep. 23, 2008.
Genbank Accession No. NC_001401.0, Adeno-associated virus-2, complete genome, Aug. 13, 2018.
GenBank Accession No. NC_006152.1, Adeno-associated virus 5, complete genome, Aug. 13, 2018.
GenBank Accession No. NC_006260.1, Adeno-associated virus-7, complete genome, Aug. 13, 2018.
GenBank Accession No. NC_006261.1, Adeno-associated virus-8, complete genome, Aug. 13, 2018.
GenBank Accession No. J01901, Adeno-associated virus 2, complete genome, Apr. 27, 1993.
GenBank Accession No. U89790.1, Adeno-associated virus 4, complete genome, Aug. 21, 2017.
GenBank Registered No. NG_011618, *Homo sapiens* titin (TTN), RefSeqGene (LRG_391) on chromosome 2, Apr. 5, 2020.
Genbank Synthetic construct *Homo sapiens* clone IMAGE:100069183, MGC:199194 anoctamin 5 (ANO5) mRNA, encodes complete protein GenBank: BC172489.1, Mar. 16, 2009.
Georganopoulou et al., "A Journey with LGMD: From Protein Abnormalities to Patient Impact", The Protein Journal, Kluwer Academic/Plenum Publishers, Dordrecht, NL, vol. 40, No. 4, Jun. 10, 2021, pp. 466-488.
Gerull et al., Identification of a novel frameshift mutation in the giant muscle filament titin in a large Australian family with dilated cardiomyopathy, J. Mal. Med. (Berl). 84:478-83 (2006).
Gerull et al., Mutations of TTN, encoding the giant muscle filament titin, cause familial dilated cardiomyopathy, Nat. Genet. 30:201-4 (2002).
Goeddel, "Gene Expression Technology: Methods in Enzymology," Academic Press, vol. 185, Jun. 11, 1990, pp. 3-7.
Gombash et al., Adeno-Associated Viral Vector Delivery to the Enteric Nervous System: a Review, Postdoc J., 2015, vol. 3, Issue 8, pp. 1-12.
Govoni et al., "Ongoing therapeutics trials and outcome measures for Duchenne muscular dystrophy", Cell Mol. Life Sci., 70:4585-602 (2013).
Graham et al., A new technique for the assay of infectivity of human adenovirus 5 DNA, Virology, 1973, vol. 52, Issue 2, pp. 456-467.

(56) References Cited

OTHER PUBLICATIONS

Gramlich et al., "Antisense-mediated exon skipping: a therapeutic strategy for titin-based dilated cardiomyopathy," EMBO Molecular Medicine, 7(5): 562-76 (2015).
Gramlich et al., "Stress-induced dilated cardiomyopathy in a knock-in mouse model mimicking human titin-based disease", J. Mal. Cell Cadiol. 47:352-8 (2009).
Granzier et al., "Deleting titin's I-band/A-band junction reveals critical roles for titin in biomechanica sensing and cardiac function", Proc. Natl. Acad. Sci. USA. 111:14589-94 (2014).
Griffin et al., Defective Membrane Fusion and Repair in Anoctamin5-Deficient Muscular Dystrophy, Human Molecular Genetics, vol. 25, No. 10, pp. 1900-1911 (Feb. 23, 2016).
Griffin et al., "Dose-Escalation of Systemically Delivered Adeno-Associated Virus-Mediated alpha-Sarcoglycan in a Mouse Model With Limb-Girdle Muscular Dystrophy Type 2D," Presented at the 2019 Muscular Dystrophy Association Clinical and Scientific Conference, Apr. 13-17, 2019. (Retrieved from: investorrelations.sarepta.com/staticfiles/8b00e773-3b86-4769-83dc-4d2bf22ffb0c).
Griffin et al., "Systemic Dose Escalation Study of Alpha-Sarcoglycan Provides Functional Improvement in SGCA (I-) Mouse Model of LGMD2D," Molecular Therapy, vol. 26, No. 5S1, May 2018, p. 166.
Grose et al., "Homologous Recombination Mediates Functional Recovery of Dysferlin Deficiency following AAV5 Gene Transfer", PLoS One, Jun. 2012, vol. 7, Issue 6, e39233.
Guilinger et al., "Fusion of catalytically inactive Cas9 to Fokl nuclease improves the specificity of genome modification," Nature Biotechnology, vol. 32, No. 6, Jun. 2014 (pp. 577-582).
Gutschner et al., "Genome engineering—Matching supply with demand," Cell Cycle, 15(11): 1395-96 2016.
Hafez et al., "Homing endonucleases: DNA scissors on a mission", Genome. 55:553-69 (2012).
Hagan, "When are mice considered old?" The Jackson Laboratory, https://www.jax.org/news-and-insights/jax-blog/2017/november/when-are-mice-considered-old# Nov. 7, 2017 (8 pages).
Hakim et al., Monitoring murine skeletal muscle function for muscle gene therapy, Methods Mal. Biol., 2011, vol. 709, pp. 75-89.
Handschin et al., Peroxisome proliferator-activated receptor gamma coactivator 1 coactivators, energy homeostasis, and metabolism, Endocrine reviews, 27:728-735 (2002).
Herman et al., "Truncations of titin causing dilated cardiomyopathy", N. Engl. J. Med. 366:619-28, 2012.
Herson et al., A phase I trial of adeno-associated virus serotype 1-gamma-sarcoglycan gene therapy for limb girdle muscular type 2C, Brain, 2012, vol. 135, Pt 2, pp. 483-492.
Hicks et al., A founder mutation in Anoctamin 5 is a major cause of limb-girdle muscular dystrophy, Brain, 134 (Pt. 1):171-82 (Jan. 2011).
Horii et al., Validation of microinjection methods for generating knockout mice by CRISPR/Cas-mediated genome engineering, Sci Rep. 4:4513 (2014).
International Application No. PCT/US19/39893, International Preliminary Report on Patentability, mailed Jan. 7, 2021, 8 pages.
International Application No. PCT/US19/39893, International Search Report and Written Opinion, mailed Sep. 25, 2019.
International Application No. PCT/US20/47339, International Preliminary Report on Patentability, mailed Mar. 3, 2022, 8 pages.
International Application No. PCT/US2016/061703, International Preliminary Report on Patentability, mailed May 15, 2018, 10 pages.
International Preliminary Report on Patentability for Appl. Ser. No. PCT/US2016/062052 dated May 22, 2018, 9 pages.
International Preliminary Report on Patentability on PCT Appl. No. PCT/US2012/066265 dated May 27, 2014 (9 pages).
International Preliminary Report on Patentability on PCT PCT/US2019/015779 dated Aug. 13, 2020 (10 pages).
International Search Report and Written Opinion for Appl. Ser. No. PCTUS2016/061703 dated Feb. 2, 2017 (13 pages).
International Search Report and Written Opinion for PCT/US2019/015779 dated Apr. 30, 2019, 14 pages.
International Search Report and Written Opinion on PCT Appl. No. PCT/US2012/066265 dated Mar. 28, 2013 (7 pages).
International Search Report and Written Opinion on PCT Appl. No. PCT/US2020/047339 dated Dec. 10, 2020 (12 pages).
International Search Report for Appl. Ser. No. PCT/US2016/062052 dated Feb. 7, 2017 (5 pages).
Itoh-Satoh et al., Titan mutations as the molecular basis for dilated cardiomyopathy, Biochem. Biophys. Res. Commun. 291:385-93 (2002).
Jaber et al., Titin isoforms, extracellular matrix, and global chamber remodeling in experimental dilated cardiomyopathy: functional implications and mechanistic insight, Circ. Heart Fail. 1:192-9 (2008).
Jinek et al., "A Programmable Dual-RNA-Guided DNA Endonuclease in Adaptive Bacterial Immunity," Science, Aug. 17, 2012, 337(6096):816-821.
Judge et al., "Design of noninflammatory synthetic siRNA mediating potent gene silencing in vivo," Molecular Therapy, 2006, vol. 13 (pp. 494-505).
Justison et al., Percutaneous assisted venous return isolated limb perfusion, J. Extra Corpor. Technol., 2009, vol. 41, Issue 4, pp. 231-234.
Kajigaya et al., Self-assembled B19 parvovirus caps ids, produced in a baculovirus system, are antigenically and immunogenically similar to native virions, Proc. Natl. Acad. Sci. USA, 88(11):4646-50 (Jun. 1991).
Kariko et al., "Suppression of RNA recognition by Toll-like receptors: the impact of nucleoside modification and the evolutionary origin of RNA," Immunity, Aug. 2005, vol. 23 (pp. 165-175).
Kennell, "Principles and Practices of Nucleic Acid Hybridization," Progress in Nucleic Acid Research and Molecular Biology, Academic Press, vol. 11, 1971, (pp. 259-301).
Kent et al., "Mechanism of microhomology-mediated end-joining promoted by human DNA polymerase theta", Nat. Struct. Mol. Biol. 22:230-237 (2015).
Kirnbauer et al., Virus-like particles of bovine papillomavirus type 4 in prophylactic and therapeutic immunization, Virology, 219(1 ):37-44 (May 1996).
Kleinstiver et al., The I-Tevl nuclease and linker domains contribute to the specificity of monomerh TALENs, G3 (Bethesda). 4:1155-65 (2014).
Kole et al., "RNA therapeutics: beyond RNA interference and antisense oligonucleotides", Nat Rev Drug Discov. Jan. 20, 2012;11(2):125-40. doi: 10.1038/nrd3625.
Kolmerer et al., "Genomic organization of M line titin and its tissue-specific expression in two distinct isoforms", J. Mol. Biol. 256:556-63 (1996).
Kormann et al., "Expression of therapeutic proteins after delivery of chemically modified mRNA in mice," Nature Biotechnology, Feb. 2011, vol. 29, No. 2 (pp. 154-157).
Kornberg et al., "The early history of DNA polymerase: a commentary by Arthur Kornberg", Biochimica et Biophysica Acta. 1000:53-56 (1989).
Kotin et al., "Manufacturing Clinical Grade Recombinant Adeno-Associated Virus Using Invertebrate Cell Lines," Human Gene Therapy, 28(4):Abstract Only, (Apr. 1, 2017).
Kramerova et al., "Null mutation of calpain 3 {p94) in mice causes abnormal sarcomere formation in vivo and in vitro", Hum. Mol. Genet., 13(13):1373-1388 (2004).
Kramerova et al., Failure to up-regulate transcription of genes necessary for muscle adaptation underlies limb girdle muscular dystrophy 2A calpainopathy, Hum. Mol. Genet., 25(11):2194-2207 (2016).
Labeit et al., "Titins: giant proteins in charge of muscle ultrastructure and elasticity", Science. 270:293-6 (1995).
Lewinter et al., Cardiac titin and heart disease, J. Cardiovasc. Pharmacol. 63:207-12 (2014).
Lewinter, "Titin isoforms in heart failure: are there benefits to supersizing", Circulation. 110:109-11 2004.

(56) References Cited

OTHER PUBLICATIONS

Li et al., "Modularly assembled designer TAL effector nucleases for targeted gene knockout and gene replacement in eukaryotes," Nucleic Acids Research, 2011, vol. 39, No. 14 (pp. 6315-6325).
Li et al., Electrical impedance myography for the in vivo and ex vivo assessment of muscular dystrophy (mdx) mouse muscle, Muscle Nerve, 49(6):829-35 (Jun. 2014).
Li et al., Electrophysiologic biomarkers for assessing disease progression and the effect of riluzole in SOD1 G93A ALS mice, PLoS One, 8(6):e65976 (Jun. 2013).
Li et al., Intracoronary administration of cardiac stem cells in mice: a new, improved technique for cell therapy in murine models, Basic Res. Cardiol. 106:849-64 (2011).
Lin et al., Transcriptional co-activator PGC-1 alpha drives the formation of slow-twitch muscle fibres, Nature, 418:797-801 (2002).
Liu et al., "Validated Zinc Finger Protein Designs for All 16 GNN DNA Triplet Targets," The Journal of Biological Chemistry, Feb. 8, 2002, vol. 277, No. 6 (pp. 3850-3856).
Louis et al., "EM_EST:BE676391", Jan. 27, 2011 (Jan. 27, 2011), XP055708767, Retrieved from the Internet: URL:http://ibis.internal.epo.org/exam/dbfetch.jsp?id=EM_EST:BE676391 [retrieved on Jun. 25, 2020].
Ma et al., Pol III Promoters to express small RNAs: Delineation of transcription initiation, Mol. Ther. Nucleic Acids. 3:e161 (2014).
Mahmood et al., "Limb-girdle muscular dystrophies: Where next after six decades from the first proposal (review)," Molecular Medicine reports, 2014, vol. 9 (pp. 1515-1532).
Mak et al., "The crystal structure of TAL effector PthXo1 bound to its DNA target," Science, Feb. 10, 2012, vol. 335, No. 6069 (pp. 716-719).
Makarenko et al., Passive stiffness changes caused by upregulation of compliant titin isoforms in human dilated cardiomyopathy hearts, Gire. Res. 95:708-16 (2004).
Martin et al., Overexpression of Galgt2 in skeletal muscle prevents injury resulting from eccentric contractions in both mdx and wild-type mice, Am. J. Physiol. Cell Physiol., vol. 296, pp. 476-488, Dec. 24, 2008.
Mashiko et al., Generation of mutant mice by pronuclear injection of circular plasmid expressing Cas9 and single guided RNA, Sci. Rep. 3:3355 (2013).
Mateos-Gomez et al., Mammalian Polymerase theta promotes alternative-NHEJ amd suppresses recombination, Nature. 518:254-257 (2015).
McCarty et al., Self-complementary AAV Vectors; Advances and Applications, Molecular Therapy, 2008, vol. 16, Issue 10, pp. 1648-1656.
Mcnally et al., "Mild and Severe Muscular Dystrophy Caused by a Single gamma-Sarcoglycan Mutation", American Journal of Human Genetics, Nov. 1996, vol. 59, No. 5, pp. 1040-1047.
McNally et al., The genetic landscape of cardiomyopathy and its role in heart failure, Cell. Metab. 21:174-182 (2015).
Mendell et al., "Gene Therapy for Muscular Dystrophy: Lessons Learned and Path Forward", Neuroscience Letters, vol. 527, No. 2, Oct. 2012, 21 pages.
Mendell et al., "Limb-girdle muscular dystrophy type 2D gene therapy restores alpha-sarcoglycan and associated proteins," Ann. Neural., 2009, vol. 66 Issue 3, pp. 290-297.
Mendell et al., Gene Delivery for Limb-Girdle Muscular Dystrophy Type 2D by Isolated Limb Infusion, Human Gene Therapy, 2019, vol. 30, Issue 7, pp. 794-801.
Mingozzi et al. "Therapeutic in vivo gene transfer for genetic disease using AAV: progress and challenges", Nature Reviews Genetics, May 2011, vol. 12 (pp. 341-355).
Monjaret et al., "The Phenotype of Dysferlin-Deficient Mice is not Rescued by Adeno-Associated Virus-Medicated Transfer of Anoctamin 5," Human Gene Therapy Clinical Development, 24(2):65-76 (Jun. 1, 2013).
Moscou et al., "A Simple Cipher Governs DNA Recognition by TAL Effectors", Science, Dec. 11, 2009, vol. 326 (p. 1501).
NCBI Accession No. NG_051363.1, *Homo sapiens* TTN antisense RNA 1 (TTN-AS1), RefSeqGene on chromosome 2, dated Feb. 17, 2020.
NCBI Accession No. XM_012650762.1, Predicted: Propithecus coquereli titin (TTN), mRNA, dated Jun. 1, 2015.
NCBI Accession No. XM_024453100.1, Predicted: *Homo sapiens* titin (TTN), transcript variant X12, mRNA, dated Mar. 1, 2020.
NCBI Blast Tool: Pairwise Similarity 1, Instant App ('488) Seq Id No. 1 [1-3977]:: U.S. Pat. No. 9981049B2 Seq Id No. 8 (CAPN3) (2024).
NCBI Blast Tool: Pairwise Similarity 2, Instant App ('488) Seq Id No. 1 [1107-3572]:: U.S. Pat. No. 9981049B2 Seq Id No. 8 (CAPN3) (2024).
NCBI Reference Sequence: "anoctamin-5 isoform a [*Homo sapiens*]", GenPept, Mar. 15, 2015, NP_998764.1.
NCBI, GenBank accession No. U34976.1 (Nov. 8, 1995), 2 pages.
Noguchi S, "Human gamma-sarcoglycan mRNA, complete cds.", NCBI, (Nov. 8, 1995), Database accession No. U34976, 2 pages.
Obermann et al., Molecular structure of the sarcomeric M band: mapping of titin and myosin binding domains in myomesin and the identification of a potential regulatory phosphorylation site in myomesin, EMBO J. 16:211-20 (1997).
Pacak et al., Long-term Skeletal Muscle Protection After Gene Transfer in a Mouse Model of LGMD-2D, Molecular Therapy, 2007, vol. 15, Issue 10, pp. 1775-1781.
Pavlovicova et al., Structure and composition of tubular aggregates of skeletal muscle fibres, Gen. Physiol. Biophys., 22(4):425-40 (Dec. 2003).
Payne et al., Nutritional therapy improves function and complements corticosteroid intervention in mdx mice. Muscle Nerve. Jan. 2006; 33(1):66-77.
Peer et al., Special delivery: targeted therapy with small RNAs, Gene. Ther. 18:1127-33 (2011).
Peled et al., Titin mutation in familial restrictive cardiomyopathy, Int. J. Cardiol. 171:24-30 (2014).
Penttila et al., Eight new mutations and the expanding phenotype variability in muscular dystrophy caused by ANOS, Neurology, 78(12):897-903 (Mar. 2012).
Powers et al., Exercise-induced oxidative stress in humans: cause and consequences, Free Radic. Biol. Med., 51 (5):942-50 (Sep. 2011 ).
Pozsgai et al., "506. [beta]—Sarcoglycan Gene Transfer Prevents Muscle Fibrosis and Inflammation in an Aged LGMD2E Mouse Model," Molecular Therapy, vol. 23 Supplement 1, May 2015, 2 pages.
Ran et al., "In vivo genome editing using *Staphylococcus aureus* Cas9," Nature, April, 9, 2015, vol. 520, (18 pages).
Richard et al., "Mutations in the Proteolytic Enzyme Calpain 3 Cause Limb-Girdle Muscular Dystrophy Type 2A", Cell, 81(1):27-40 (1995).
Roberts et al., Integrated allelic, transcriptional, and phenomic dissection of the cardiac effects of titin truncations in health and disease, Sci. Transl. Med. 7:270ra6 (2015).
Rodino-Klapac et al., "Micro-dystrophin and follistatin co-delivery restores muscle function in aged DMD model," Human Molecular Genetics, Dec. 2013, vol. 22, No. 24 (pp. 4929-4937).
Rodino-Klapac et al., Demonstration of SGCA Expression and Related Outcomes in Phase I/IIa Safety Isolated Limb Perfusion Trial in LGMD2D Subjects, Molecular Theerapy, 2018, vol. 26, Issue 5, Supplemental 1, p. 1, Abstract No. 250.
Rose, comprehensive Virology 3:1-61 (1974).
Roudaut et al., "Restriction of Calpain3 Expression to the Skeletal Muscle Prevents Cardiac Toxicity and Corrects Pathology in a Murine Model of Limb-Girdle Muscular Dystrophy", Circulation, 128(10): 1094-1104, (Sep. 2013).
Rutledge et al., Infectious clones and vectors derived from adeno-associated virus (AAV) serotypes other than AAV type 2, J. Viral., 7291):309-19 (Jan. 1998).
Sahenk et al., Systemic delivery of AAVrh74.tMCK.hCAPN3 rescues the phenotype in a mouse model for LGMD2A/R1, Mol. Ther. Methods Clin. Dev., 22:401-414 (2021).
Sambrook et al., Cold spring harbor laboratory press, cold Spring Harbor, N.Y., (2001).

(56) References Cited

OTHER PUBLICATIONS

Sambrook et al., Molecular Cloning: a Laboratory Manual, 2 edition (1989).
Sander et al., CRISPR-Cas systems for editing, regulating and targeting genomes, Nat. Biotechnol. 32:347-55 (2014).
Sanganalmath et al., Cell therapy for heart failure: a comprehensive overview of experimental and clincal studes, current challenges, and future directions, Gire. Res. 113:810-34 (2013).
Sarepta Therapeutics: "Sarepta Therapeutics' Investigational Gene Therapy SRP-9003 for the Treatment of Limb-Girdle Muscular Dystrophy Type 2E Shows Sustained Expression and Functional Improvements 2 Years After Administration", Mar. 18, 2021, pp. 1-3, Retrieved from the Internet: URL: https://investorrelations.sarepta.com/news--releases/news-release--details/sarepta-therapeutics--investigational-gene-therapy-srp-9003-0 [retrieved on Jun. 23, 2023].
Schreiber et al., The transcriptional coactivator PGC-1 regulates the expression and activity of the orphan nuclear receptor estrogen-related receptor alpha (ERRalpha), J. Biol. Chem., 278: 9013-9018 (2003).
Segal et al., "Toward controlling gene expression at will: Selection and design of zinc finger domains recognizing each of the 5'-GNN-3' DNA target sequences," Proceedings of the National Academy of Sciences, USA, Mar. 1999, vol. 96 (pp. 2758-2763).
Shih et al., Finding the Achilles' heel of Muscle Giant-TALEN-mediated Gene-editing in Zebrafish Titin, Circulation Research, Oct. 21, 2015, vol. 117, no.(suppl_1), pp. A344. DOI: https://doi.org/10.1161/res.117.suppl_1.344.
Siu et al., Familial dilated cardiomyopathy locus maps to chromosome 2q31, Circulation. 99:1022-6 (1999).
Smith et al., Modification and secretion of human interleukin 2 produced in insect cells by a baculovirus expression vector, Proc. Natl. Acad. Sci. USA, 82(24):8404-8 (1985).
Sondergaard et al., "AAV.Dysferlin Overlap Vectors Restore Function in Dysferlinopathy Animal Models," Annals of Clinical and Translational Neurology, 2015, vol. 2, Issue 3, pp. 256-270.
Sonntag et al., A viral assembly factor promotes AAV2 capsid formation in the nucleolus, PNAS,2010, vol. 107, Issue 22, pp. 10220-10225.
Sorimachi et al., Tissue-specific expression and alpha-actinin binding properties of the Z-disc titin: implications for the nature of vertebrate Z-discs, J. Mal. Biol. 270:688-95 (1997).
Soutschek et al., "Therapeutic silencing of an endogenous gene by systemic administration of modified siRNAs," Nature, Nov. 2004, pp. 173-178, vol. 432.
Steentoft et al., Precision genome editing: a small revolution for glycobiology, Glycobiology. 24:663-80 (2014).
Strobel, et al. "Antioxidant Supplementation Reduces Skeletal Muscle Mitochondrial Biogenesis", Official Journal of the American College of Sports Medicine, 2011, pp. 1017-1024.
Thiruvengadam et al., "Anoctamin 5 Knockout Mouse Model Recapitulates LGMD2L Muscle Pathology and Offers Insight Into in vivo Functional Deficits," Journal of Neuromuscular Diseases, 2021, vol. 8 (S243-S255).
Torella, et al., "Cardiovascular development: towards biomedical applicability; Resident cardiac stem cells", CMLS Cellular and Molecular Life Sciences 64(6): 661-673 (2007).
Tsai et al., "GUIDE-seq enables genome-wide profiling of off-target cleavage by CRISPR-Cas nucleases," Nature Biotechnology, Feb. 2015, vol. 33, No. 2 (pp. 187-197).
Tsai et al., Dimeric CRISPR RNA-guided Fokl nucleases for highly specific genome editing, Nat. Biotechnol. 32:569-76 (2014).
Van Akkooi et al., Isolated limb perfusion for an irresectable melanoma recurrence in a Jehovah's witness, Eur. J. Cardiothorac. Surg., 2006, vol. 30, Issue 2, pp. 408-410.
Volkov et al., Selective protection of nuclease-sensitive sites in siRNA prolongs silencing effect, Oligonucleotides. 19:191-202 (2009).
Wang et al., "The potential of adeno-associated viral vectors for gene delivery to muscle tissue", Exp. Opin. on Drug. Del., 11(3):345-364 (2014).
Wang et al., Rapid and efficient assembly of transcription activator-like effector genes by USER cloning, J. Genet. Genomics. 41:339-47 (2014).
Wang et al., Recombinant AAV serotype 1 transduction efficiency and tropism in the murine brain, Gene Ther., 2003, vol. 10, Issue 17, pp. 1528-1534.
Watson et al., "Recombinant DNA," Scientific American, Second Edition, 2001 (pp. 153-154).
Weber et al., "A Modular Cloning System for Standardized Assembly of Multigene Constructs," Feb. 2011, vol. 6, No. 2, e16765 (11 pages).
Whitehead et al., Silencing or stimulation? siRNA delivery and the immune system, Annual Review of Chemical and Biomolecular Engineering. 2:77-96 (2011).
Wikipedia, "Adeno-associated virus," downloaded Dec. 29, 2017 (pp. 1-18).
Wikipedia, "Limb-girdle muscular dystrophy," 11 pages, Retrieved Oct. 26, 2023, from https://en.wikipedia.org/wiki/Limb-girdle_muscular_dystrophy (11 pages).
Winkler, Oligonucleotide conjugates for therapeutic applications, Ther. De/iv. 4:791-809 (2013).
Witting et al: "Anoctamin 5 muscular dystrophy in Denmark: prevalence, genotypes, phenotypes, cardiac findings, and muscleprotein expression", Case Reports, May 14, 2013, PMID: 23670307 DOI: 10.1007/s00415-013-6934-y.
Wolfs et al., MegaTevs: single-chain dual nucleases for efficient gene disruption, Nucliec Acids Res. 42:8816-29 (2014).
Wu et al., Mutational analysis of the adeno-associated virus type 2 (AAV2) capsid gene and construction of AAV2 vectors with altered tropism, J. Viral., 74(18):8635-47 (Sep. 2000).
Xu et al., "Genetic disruption of Ano5 in mice does not recapitulate human ANO5-deficient muscular dystrophy," Skeletal Muscle, 2015, vol. 5, No. 43 (pp. 1-14).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 2007, vol. 17, Issue 3, pp. 209-220.
Yalvac et al., Impaired regeneration in calpain-3 null muscle is associated with perturbations in mTORC1 signaling and defective mitochondrial biogenesis, Skelet. Muscle, 7:27, 18 pages (2017).
Yan et al., Inverted terminal repeat sequences are important for intermolecular recombination and circularization of adeno-associated virus genomes, J. Viral., 79(1 ):364-79 (Jan. 2005).
Yuasa et al., "Gene therapy of muscular dystrophy: Systemic gene delivery to skeletal muscles" Jan. 2007, Drug Delivery System 22(2):140-147, doi.org/10.2745/dds.22.140 (English Abstract).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zhao et al., BPV1 E2 protein enhances packaging of full-length plasmid DNA in BPV1 pseudovirions, Virology, 272(2):382-93 (Jul. 2000).
Zhou et al., Pressure Overload by Transverse Aortic Constriction Induces Maladaptive Hypertrophy in a Titin-Truncated Mouse Model, Biomed. Res. Int. 2015:163564 (2015).
Zou et al., "An internal promoter underlies the difference in disease severity between N- and C-terminal truncation mutations of Titin in zebrafish", eLife, Oct. 16, 2015, vol. 4, pp. e09406. DOI:https://doi.org/10.7554/eLife.09406.
Kotin et al., Manufacturing Clinical Grade Recombinant Adena-Associated Virus Using Invertebrate Cell Lines, Hum. Gene Ther., 28(4):350-360 (2017).
Laughlin et al., Cloning of infectious adeno-associated virus genomes in bacterial plasmids, Gene., 23(1):65-73 (1983).
Laws et al., Progression of kyphosis in mdx mice, J. Appl. Physiol. 97:1970-7 (2004).
Lebkowski et al., Adena-associated virus: a vector system for efficient introduction and integration of DNA into a variety of mammalian cell types, Mol. Cell. Biol. 8:3988-96 (1988).
Lewis et al., Generation of neutralizing activity against human immunodeficiency virus type 1 in serum by antibody gene transfer, J. Virol., 76(17):8769-8775 (2002).

(56) References Cited

OTHER PUBLICATIONS

Liu et al., Adeno-associated virus-mediated microdystrophin expression protects young mdx muscle from contraction-induced injury, Mol. Ther., 11(2):245-256 (2005).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector design Tour de Force: integrating combinatorial and rational approaches to derive novel adeno-associated virus variants, Molecular Therapy, 22(11):1900-1909 (2014).
Matsuda et al., Visualization of dystrophic muscle fibers in mdx mouse by vital staining with Evans blue: evidence of apoptosis in dystrophin-deficient muscle, J. Biochem., 118(5):959-964 (1995).
Mccarty et al., Adeno-associated virus terminal repeat (TR) mutant generates self-complementary vectors to overcome the rate-limiting step to transduction in vivo, Gene. Ther., 10(26):2112-2118 (2003).
Mccarty et al., Self-complementary recombinant adeno-associated virus (scAAV) vectors promote efficient transduction independently of DNA synthesis, Gene. Ther., 8(16):1248-1254 (2001).
Mclaughlin et al., Adeno-associated virus general transduction vectors: analysis of proviral structures, J. Virol., 62(6):1963-73 (1988).
Meadows et al., Micro-RNA-29 Overexpression by adeno-associated virus suppresses fibrosis in mdx:utrn+/− Mice (S61.003), Neurology. 82:S61.003 (Abstract) (2014).
Meadows et al., Reducing Skeletal Muscle Fibrosis with AAV-Delivered miR-29 (P04.089), Neural., 1 Supplement, (2012).
Melacini et al., Heart involvement in muscular dystrophies due to sarcoglycan gene mutations, Muscle Nerve, 22(4):473-479 (1999).
Mendell et al., A phase I/2a follistatin gene therapy trial for becker muscular dystrophy, Mol. Ther., 23(1):192-201 (2015).
Mendell et al., Gene Therapy for Spinal Muscular Atrophy Type 1 Shows Potential to Improve Survival and Motor Functional Outcomes, Mol. Ther. 24:S190 (2016).
Mendell et al., Single-Dose Gene-Replacement Therapy for Spinal Muscular Atrophy, N. Engl. J. Med., 377:1713-1722 (2017).
Merten, AAV vector production: state of the art developments and remaining challenges, Cell Gene Therapy Insights, 2(5):521-551 (2016).
Moore et al., Limb-girdle muscular dystrophy in the United States, J. Neuropathol. Exp. Neurol., 65(10):995-1003 (2006).
Moorwood et al., Isometric and eccentric force generation assessment of skeletal muscles isolated from murine models of muscular dystrophies, Journal of Visualized Experiments. 71:e50036 (2013).
Mori et al., Two novel adeno-associated viruses from cynomolgus monkey: pseudotyping characterization of capsid protein, Virology, 330(2):375-383 (2004).
Murphy et al., Long-term correction of obesity and diabetes in genetically obese mice by a single intramuscular injection of recombinant adeno-associated virus encoding mouse leptin, Proc. Natl. Acad. Sci. USA, 94(25):13921-13926 (1997).
Muscat et al., Multiple 5'-flanking regions of the human alpha-skeletal actin gene synergistically modulate muscle-specific expression, Mol. Cell. Biol., 7(11):4089-4099 (1987).
Muzyczka, Use of Adeno-Associated Virus as a General Transduction Vector for Mammalian Cells, Current Topics in Microbiology and Immunology, 158:97-129 (1992).
Narayanaswami et al., Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine, Neurology, 83(16):1453-1463 (2014).
Paul et al., Increased Viral Titer Through Concentration of Viral Harvests from Retroviral Packaging Lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Pozsgai et al., 172. Pre-Clinical Efficacy Study of Beta- Sarcoglycan Gene Transfer, Malec. Ther., 21(1):s68 (2013).
Pozsgai et al., Beta-Sarcoglycan Gene Transfer Leads to Functional Improvement in a Model of LGMD2E (S61.002), Neur., 82(10):1-3 (2014).
Pozsgai et al., β-Sarcoglycan gene transfer decreases fibrosis and restores force in LGMD2E mice, Gene. Ther., 23(1):57-66 (2016).
Pozsgai et al., Systemic AAV-mediated (Beta)-sarcoglycan delivery targeting cardiac and Skeletal muscle ameliorates histological and functional deficits in LGMD2E mice, Mol. Ther. 25(4):855-869 (2017).
Rabinowitz et al., Cross-packaging of a single adeno-associated virus (AAV) type 2 vector genome into multiple AAV serotypes enables transduction with broad specificity, J. Virol. 76:791-801 (2002).
Rafael-Fortney et al., Early treatment with lisinopril and spironolactone preserves cardiac and skeletal muscle in duchenne muscular dystrophy mice, Circulation. 124:582-8 (2011).
Rodino-Klapac et al., A translational approach for limb vascular delivery of the micro-dystrophin gene without high vol. or high pressure for treatment of Duchenne muscular dystrophy, J. Transl. Med., 5:45-55 (2007).
Rodino-Klapac et al., Lack of toxicity of alpha-sarcoglycan overexpression supports clinical gene transfer trial in LGMD2D, Neurology, 71(4):240-247 (2008).
Rodino-Klapac et al., Persistent expression of FLAG-tagged micro dystrophin in nonhuman primates following intramuscular and vascular delivery, Mol. Ther., 18(1):109-117 (2010).
Ruffing et al., Mutations in the carboxy terminus of adeno-associated virus 2 capsid proteins affect viral infectivity: lack of an RGD integrin-binding motif Free, J. Gen. Virol., 75:3385-3392 (1994).
Salva et al., Design of tissue-specific regulatory cassettes for high-level rAAV-mediated expression in skeletal and cardiac muscle, Mol. Ther., 15(2):320-9 (2007).
Sambrook et al., Molecular Cloning: a Laboratory Manual, Cold Spring Harbor Laboratory, Cold Spring Harbor, New York (2nd ed. 1989).
Samulski et al., Cloning of adeno-associated virus into pBR322: rescue of intact virus from the recombinant plasmid in human cells, Proc. Natl. Acad. Sci. USA, 79(6):2077-2081 (1982).
Samulski et al., Cloning of adeno-associated virus into pBR322: rescue of intact virus from the recombinant plasmid in human cells, Proc. Natl. Acad. Sci. USA. 79:2077-81 (1982).
Samulski et al., Helper-free stocks of recombinant adeno-associated viruses: normal integration does not require viral gene expression, J. Virol., 63(9):3822-3828 (1989).
Sandona et al., Sarcoglycanopathies: molecular pathogenesis and therapeutic prospects, Exp Rev. Mol. Med. 11:e28 (2009).
Schenpp et al., Highly purified recombinant adeno-associated virus vectors. Preparation and quantitation, Methods Mol. Med., 69:427-443 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Semplicini et al., Clinical and genetic spectrum in limb-girdle muscular dystrophy type 2E, Neurology. 84:1772-81 (2015).
Senapathy et al., Molecular cloning of adeno-associated virus variant genomes and generation of infectious virus by recombination in mammalian cells, J. Biol. Chem., 259:4661-4666 (1984).
Shield et al., E-box sites and a proximal regulatory region of the muscle creatine kinase gene differentially regulate expression in diverse skeletal muscles and cardiac muscle of transgenic mice, Mol. Cell. Biol., 16(9):5058-5068 (1996).
Agbandje-McKenna et al., "AAV Capsid Structure and Cell Interactions", Adeno-Associated Virus: Methods and Protocols, in Methods in Molecular Biology, Ch. 3, 807:47-92 (2011).
Carrie et al., "Mutational diversity and hot spots in alpha-sarcoglycan gene in autosomal recessive muscular dystrophy (LGMD2D)," Journal of Medical Genetics, 34:470-475 (1997).
Hartigan-O'Connor et al., "Developments in gene therapy for muscular dystrophy," Microscopy Research and Technique 48:223-238 (2000).

(56) References Cited

OTHER PUBLICATIONS

Pozsgai, E.R., Adeno-Associated Virus Mediated β-Sarcoglycan Gene Replacement Therapy for the Treatmentof Limb Girdle Muscular Dystrophy Type 2E [Doctoral dissertation, Ohio State University]. OhioLINK Electronic Theses and Dissertations Center. (2016) http://rave.ohiolink.edu/etdc/view?acc_num=osu147697211337827.

Fougerousse et al., "Phenotypic Correction of a-Sarcoglycan Deficiency by Intra-arterial Injection of a Muscle-specific Serotype 1 rAAV Vector," Molecular Therapy, 15(1):53-61 (Jan. 2007).

Nationwide Children's Hospital, "Phase I/IIa gene transfer clinical trial for LGMD2D using scAAVrh74.tMCK.hSGCA". Clinical Protocol, Center for Gene Therapy, https://cdn.clinicaltrials.gov/large-docs/91/NCT01976091/Prot_000.pdf (Feb. 10, 2017).

Kramerova et al., "Failure to up-regulate transcription of genes necessary for muscle adaptation underlies limb girdle muscular dystrophy 2A (calpainopathy)," Human Molecular Genetics, 25(11):2194-2207 (2016).

* cited by examiner scAAVrh.74.tMCK.hSGCA

ITR=Inverted Terminal Repeat, hSGCA=Human Alpha-Sarcoglycan, pA=Polyadenylation Sequence, AAV=Adeno-Associated Virus

Figure 2A

3'ITR

*Poly A*

SGCA Codon Optimized tMCK Promoter

5'ITR

```
   1 CTGCGCGCTC GCTCGCTCAC TGAGGCCGCC CGGGCAAAGC CCGGGCGTCG
  51 GGCGACCTTT GGTCGCCCGG CCTCAGTGAG CGAGCGAGCG CGCAGAGAGG
 101 GAGTGGCCAA CTCCATCACT AGGGGTTCCT TGTAGTTAAT GATTAACCCG
 151 CCATGCTACT TATCTACGTA GCCATGCTCT AGAGGCGCGC CCCTGCAGGA
 201 CACACAAAAA ACCAACACAC AGATCTAATG AAAATAAAGA TCTTTTATTG
 251 CGGCCTCAAT GCTGGTCCAG AATCAGTGGC ACCTGGGCGC TATCCACTCT
 301 AGGGGGCAGC CGTTCGCCAG TGTGCACATT AAACATAGGC AGTGTACTCA
 351 GTGGCCTTGG CACCTCCCTA GAAGCAGCCA TCTGGCGCAG TTCCTCGGTG
 401 TTGCCGTGAA TAGTACAATG GTGCACCATC TGGATATCAG ATGTGGCCAG
 451 GTCTCTCTTC AGCCGTCCCT CTCTCCGACA GCACATCACA TAAGCCAGCA
 501 GCAGGGTCAG CAGCAGAGCC ACCAGCAGAG GCACCAGCAG AGTCACCAGA
 551 GCGTCCACCA GGAAATCCCT GTCTGGGGCT TCTGTTGGAG GACAAAAGAA
 601 AGGATCGTGC TCCAGGATTC CGTCTCCAGG GGTTGGCACT TCGTCAGCTG
 651 GCTCAGGCAC AGATTTATCC ACCAGAGTCA CGTTGCACCA GTCCACGCGA
 701 AAATGGGGGG CCAGTGTGTC ATAACAGGAC AGCAGTGGTG GCTGTCCCTG
 751 AGCGCACCTA GCGTGACTAT CAGGAGAAGC CACCATCTTC AGGCAGGTGG
 801 AGAATGGGGA AGCGCTTCCC ACTTTAATGT ACACCCCTTC CTTCCTTCCC
 851 TCGATTGGCA GTGGCACCCT TCCTCCCCTA TCCAGAGCGC TAGTCACATT
 901 CAGCAGCTGC AGTTCTCCTG GCTCCCACAG TCCTCCCAGA GCGGACAGAA
 951 ATCTGCTGGC GGGTGTTGAT GGCAGCACTT CCTCAGCGTC GTGTGACCGC
1001 ACCAGGAACT CGGCCTGATA AGGCAGCAGG GGTCCTTCTG GATCCCCAAT
```

Figure 2B

```
1051 CTCCAGCACC AGGCGCTGCC TGGTAGTATC AAAACTGTCG CGGTTGTAAG
1101 CTGTCACTTC GATCACCTGC AGTCCCCTGT CCTCTGGGGT AGCGCTTCCA
1151 TACAGGAATC CAGGATGGTG GGGTGATCTC TGGGTGTATC TCAGCCACCG
1201 TGGCAGATCA GGATGGCCCT GCAGATGGGC GTGGTAAGTG ATATGCACAG
1251 CAGGTGGCAC AGCCACGTGT TCTGGCAGAC TCAGAAATGT CTCATGGTCC
1301 AGGGTGTGCA CGAACACCCG GCCCACCAGT GGGTGCAGTG TGGTCTGCTG
1351 AGCCTCGGTA TCTCCCAGTC CAGCCAGCAG CACCACCAGC AGAGGAGTCC
1401 AGAACAGTGT CTCGGCCATG GTGGTACCAC GCGCTGTAAT TGAACTGGGA
1451 GTGGACACCT GTGGAGAGAA AGGCAAAGTG GATGTCAGTA AGACCAATAG
1501 GTGCCTATCA GAAACGCAAG AGTCTTCTCT GTCTCGACAA GCCCAGTTTC
1551 TATTGGTCTC CTTAAACCTG TCTTGTAACC TTGATACTTA CCTGCCCAGT
1601 GCCTCACGAC CAACTTCTGC AGGTGACCCG GGGGCAGCCC CTGTGCCCCT
1651 GGGTTATATA GAGGAGCCTA CAGGGTGTGA CTAGCCAGGA GGGGCTGTCC
1701 CCAGGGAGGA CCAGGGACAG GGTTATTTTT AGAGCGAGCT TCTCCTCCAT
1751 GGTGTACAGA GCCTAAGACC CAGGCACCGG GGTGGGGTAA CCGCTCAGGC
1801 TCAGGCAGCA GGTGTTGGGG GGGGGGGGCA GCAGGTGTTG GGGTTAATTA
1851 TAACCAGGCA TCTCGGGTGT CCCCAGGCCT TGCCTCCTTA CATGGGCAGC
1901 CTAGACCCGT AGTGGTCCAC CAGGGACAGG GTTATTTTTA GAGCGAGCTT
1951 CTCCTCCATG GTGTACAGAG CCTAAGACCC AGGCACCGGG GTGGGGTAAC
2001 CGCTCAGGCT CAGGCAGCAG GTGTTGGGGG GGGGGGGGCA GCAGGTGTTG
2051 GGGTTAATTA TAACCAGGCA TCTCGGGTGT CCCCAGGCCT TGCCTCCTTA
2101 CATGGGCAGC ATAGACCCGT AGTGGATCCA CCAGGGACAG GGTTATTTTT
2151 AGAGCGAGCT TCTCCTCCAT GGTGTACAGA GCCTAAGACC CAGGCACCGG
2201 GGTGGGGTAA CCGCTCAGGC TCAGGCAGCA GGTGTTGGGG GGGGGGGGGC
2251 AGCAGGTGTT GGGGTTAATT ATAACCAGGC ATCTCGGGTG TCCCCAGGCC
2301 TTGCCTCCTT ACATGGGCAG CCTAGACCCG TAGTGGGGCA TGCAAGTTTG
2351 CGGCCGCCAA TTGGTTAACC CCACTCCCTC TCTGCGCGCT CGCTCGCTCA
2401 CTGAGGCCGC CCGGGCAAAG CCCGGGCGTC GGGCGACCTT TGGTCGCCCG
```

Figure 2C

```
2451 GCCTCAGTGA GCGAGCGAGC GCGCAGAGAG GGAGTGGGGT TAACCAATTG
2501 GCGGCCGCAA ACTTGCATGC CCCACTACGG GTCTAGGCTG CCCATGTAAG
2551 GAGGCAAGGC CTGGGGACAC CCGAGATGCC TGGTTATAAT TAACCCCAAC
2601 ACCTGCTGCC CCCCCCCCCC CAACACCTGC TGCCTGAGCC TGAGCGGTTA
2651 CCCCACCCCG GTGCCTGGGT CTTAGGCTCT GTACACCATG GAGGAGAAGC
2701 TCGCTCTAAA AATAACCCTG TCCCTGGTGG ATCCACTACG GGTCTATGCT
2751 GCCCATGTAA GGAGGCAAGG CCTGGGGACA CCCGAGATGC CTGGTTATAA
2801 TTAACCCCAA CACCTGCTGC CCCCCCCCCC CCAACACCTG CTGCCTGAGC
2851 CTGAGCGGTT ACCCCACCCC GGTGCCTGGG TCTTAGGCTC TGTACACCAT
2901 GGAGGAGAAG CTCGCTCTAA AAATAACCCT GTCCCTGGTG GACCACTACG
2951 GGTCTAGGCT GCCCATGTAA GGAGGCAAGG CCTGGGGACA CCCGAGATGC
3001 CTGGTTATAA TTAACCCCAA CACCTGCTGC CCCCCCCCCC CAACACCTGC
3051 TGCCTGAGCC TGAGCGGTTA CCCCACCCCG GTGCCTGGGT CTTAGGCTCT
3101 GTACACCATG GAGGAGAAGC TCGCTCTAAA AATAACCCTG TCCCTGGTCC
3151 TCCCTGGGGA CAGCCCCTCC TGGCTAGTCA CACCCTGTAG GCTCCTCTAT
3201 ATAACCCAGG GGCACAGGGG CTGCCCCCGG GTCACCTGCA GAAGTTGGTC
3251 GTGAGGCACT GGGCAGGTAA GTATCAAGGT TACAAGACAG GTTTAAGGAG
3301 ACCAATAGAA ACTGGGCTTG TCGAGACAGA GAAGACTCTT GCGTTTCTGA
3351 TAGGCACCTA TTGGTCTTAC TGACATCCAC TTTGCCTTTC TCTCCACAGG
3401 TGTCCACTCC CAGTTCAATT ACAGCGCGTG GTACCACCAT GGCCGAGACA
3451 CTGTTCTGGA CTCCTCTGCT GGTGGTGCTG CTGGCTGGAC TGGGAGATAC
3501 CGAGGCTCAG CAGACCACAC TGCACCCACT GGTGGGCCGG GTGTTCGTGC
3551 ACACCCTGGA CCATGAGACA TTTCTGAGTC TGCCAGAACA CGTGGCTGTG
3601 CCACCTGCTG TGCATATCAC TTACCACGCC CATCTGCAGG GCCATCCTGA
3651 TCTGCCACGG TGGCTGAGAT ACACCCAGAG ATCACCCCAC CATCCTGGAT
3701 TCCTGTATGG AAGCGCTACC CCAGAGGACA GGGGACTGCA GGTGATCGAA
3751 GTGACAGCTT ACAACCGCGA CAGTTTTGAT ACTACCAGGC AGCGCCTGGT
3801 GCTGGAGATT GGGGATCCAG AAGGACCCCT GCTGCCTTAT CAGGCCGAGT
```

Figure 2D

3851 TCCTGGTGCG GTCACACGAC GCTGAGGAAG TGCTGCCATC AACACCCGCC

3901 AGCAGATTTC TGTCCGCTCT GGGAGGACTG TGGGAGCCAG GAGAACTGCA

3951 GCTGCTGAAT GTGACTAGCG CTCTGGATAG GGGAGGAAGG GTGCCACTGC

4001 CAATCGAGGG AAGGAAGGAA GGGGTGTACA TTAAAGTGGG AAGCGCTTCC

4051 CCATTCTCCA CCTGCCTGAA GATGGTGGCT TCTCCTGATA GTCACGCTAG

4101 GTGCGCTCAG GGACAGCCAC CACTGCTGTC CTGTTATGAC ACACTGGCCC

4151 CCCATTTTCG CGTGGACTGG TGCAACGTGA CTCTGGTGGA TAAATCTGTG

4201 CCTGAGCCAG CTGACGAAGT GCCAACCCCT GGAGACGGAA TCCTGGAGCA

4251 CGATCCTTTC TTTTGTCCTC CAACAGAAGC CCCAGACAGG GATTTCCTGG

4301 TGGACGCTCT GGTGACTCTG CTGGTGCCTC TGCTGGTGGC TCTGCTGCTG

4351 ACCCTGCTGC TGGCTTATGT GATGTGCTGT CGGAGAGAGG GACGGCTGAA

4401 GAGAGACCTG GCCACATCTG ATATCCAGAT GGTGCACCAT TGTACTATTC

4451 ACGGCAACAC CGAGGAACTG CGCCAGATGG CTGCTTCTAG GGAGGTGCCA

4501 AGGCCACTGA GTACACTGCC TATGTTTAAT GTGCACACTG GCGAACGGCT

4551 GCCCCCTAGA GTGGATAGCG CCCAGGTGCC ACTGATTCTG GACCAGCATT

4601 GA*GGCCGCAA TAAAAGATCT TTATTTTCAT TAGATCTGTG TGTTGGTTTT*

4651 *TTGTG*TGTCC TGCAGGGGCG CGCCTCTAGA GCATGGCTAC GTAGATAAGT

4701 AGCATGGCGG GTTAATCATT AACTACAAGG AACCCCTAGT GATGGAGTTG

4751 GCCACTCCCT CTCTGCGCGC TCGCTCGCTC ACTGAGGCCG GGCGACCAAA

4801 GGTCGCCCGA CGCCCGGGCT TTGCCCGGGC GGCCTCAGTG AGCGAGCGAG

4851 CGCGCAG

SELF-COMPLEMENTARY ADENO-ASSOCIATED VIRUS VECTOR AND ITS USE IN TREATMENT OF MUSCULAR DYSTROPHY

This application claims priority benefit of U.S. Provisional Application No. 63/284,418 filed Nov. 30, 2021, which is incorporated herein by reference in its entirety.

INCORPORATION BY REFERENCE OF MATERIAL SUBMITTED ELECTRONICALLY

This application contains, as a separate part of the disclosure, a Sequence Listing in computer-readable form which is infreferecorporated by reference in its entirety and identified as follows: Filename: 56757_Seqlisting.txt; Size: 24, 131 bytes; Created: Nov. 9, 2022.

FIELD OF THE INVENTION

Described herein are therapy vectors such as AAV vectors expressing alpha-sarcoglycan and method of using these vectors to reduce and prevent fibrosis in subjects suffering from a muscular dystrophy, e.g. limb girdle muscular dystrophies (LGMD) such as LGMD2D.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One group of MDs is the limb girdle muscular dystrophies (LGMD). LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

Specialized tests for LGMD are now available through a national scheme for diagnosis, the National Commissioning Group (NCG).

LGMD subtype 2D (LGMD2D), often referred to as α-sarcoglycanopathy, is an autosomal recessive disorder caused by mutations in the alpha-sarcoglycan gene (SGCA; alpha-sarcoglycan), leading to complete or reduced loss of functional protein with loss of other structural components of the dystrophin-associated protein complex. Notably, loss of the alpha-sarcoglycan protein leads to a progressive muscular dystrophy with deteriorating muscle function, with an onset from 3 to 8 years of age. Symptoms include: delayed ambulation, weakness in proximal muscles caused by fat replacement and fibrosis, elevated creatine kinase, scoliosis, and joint contractures. The debilitating disease often leads to wheelchair dependency and death due to respiratory failure. Thus, there remains a need for treatments for LGMD2D.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Functional improvement in patients suffering from LGMD and other muscular dystrophies require both gene restoration and reduction of fibrosis. There is a need for methods of reducing fibrosis that may be paired with gene restoration methods for more effective treatments of LGMD and other muscular dystrophies.

SUMMARY

Described herein are gene therapy vectors, e.g. AAV, expressing the alpha-sarcoglycan gene and methods of delivering alpha-sarcoglycan to the muscle to reduce and/or prevent fibrosis; and/or to increase muscular force, and/or to treat a mammalian subject suffering from muscular dystrophy.

Provided herein are self-complementary AAV (scAAV) that express the alpha-sarcoglycan gene. For example, the provided scAAV comprise a polynucleotide sequence comprising i) two nucleotide sequence encoding the alpha-sarcoglycan protein which are self complementary, ii) two polyadenylation sequences which are self complementary and a comprises a mutated inverted terminal repeat (ITR) located in center of the AAV genome sequence (expression cassette).

Also provided is a recombinant AAV (rAAV) vector comprising a polynucleotide sequence, wherein the polynucleotide sequence comprises, from 5' to the 3' direction, (1) a complementary sequence of a polyadenylation sequence; (2) a complementary sequence of a gene of interest; (3) a complementary sequence of an intron; (4) a complementary sequence of a promoter; (5) the 5' ITR sequence; (6) the promoter; (7) the intron; (8) the gene of interest; and (9) the polyadenylation sequence; wherein the polynucleotide sequence is flanked by two 3' ITR sequences, wherein the two 3' ITR sequences are complementary to each other. In one embodiment, the gene of interest comprises human sarcoglycan-β (hSCGB), human sarcoglycan γ (hSCGG), human dysferlin, or human ANO5, or calpain-3 (Cap 3) gene. In another embodiment, the promoter is a muscle specific control element. Examples of a muscle specific control element include human skeletal actin gene element, cardiac actin gene element, myocyte-specific enhancer binding factor MEF) element, muscle creatine kinase (MCK) promoter, truncated MCK (tMCK) promoter, tMCK enhancer, myosin heavy chain (MHC) promoter, MHCK7 promoter, C5-12 promoter, murine creatine kinase enhancer element, skeletal fast-twitch troponin c gene element, slow-twitch cardiac troponin C gene element, the slow-twitch troponin I gene element, hypoxia-inducible nuclear factor binding element, or steroid-inducible element or glucocorticoid response element (GRE).

Single strand AAV vectors (ssAAV), once in the nucleus, require cell-mediated synthesis of the second strand before it is ready for replication and transcription. However, the scAAV provided herein are superior to ssAAV in gene therapy because the scAAV bypasses the rate-limiting step of the cellular synthesis of the second-strand as required in a ssAAV.

Provided herein is a polynucleotide that comprises two self complementary nucleotide sequence (also referred to as expression cassettes), wherein in each nucleotide sequence comprises a tMCK promoter, the hSGCA cDNA sequence and a polyadenylation sequence and a single 5' ITR located in between the two nucleotide sequences. The 5' ITR creates a hairpin when the nucleotide sequences hybridize.

For example, the disclosure provides for the polynucleotide sequence of SEQ ID NO: 1, which is also set out as a schematic in FIG. 1. The polynucleotide sequence of SEQ ID NO: 1 is a 4857 nucleotide sequence which comprises two hSGCA cDNA sequences (SEQ ID NO: 2 and/or SEQ ID NO: 6), which encode the amino acid sequence of SEQ ID NO: 3 and hybridize to each other, and two tMCK promoters (SEQ ID NO: 7 and/or SEQ ID NO: 9) which hybridize to each other and two polyadenyation sequences (SEQ ID NO: 5 and/or SEQ ID NO: 10) which hybridize to each other. An ITR sequence located in the center of the polynucleotide sequence has the nucleotide sequence set out as SEQ ID NO: 8. Additional ITR sequnces are set out as SEQ ID NOS: 4 and 11.

The disclosure provides for a polynucleotide sequence comprising a nucleotide sequence at least about 90%, at least about 95% or at least about 99% identical to the nucleotide sequence of SEQ ID NO: 1. The disclosure also provide for a polynucleotide sequence comprising the nucleotide sequence of SEQ ID NO: 1.

In addition, the disclosure provides for recombinant AAV (rAAV) comprising any of the disclosed polynucleotides. For example, the disclosure provides for a rAAV comprising a polynucleotide sequence comprising a nucleotide sequence at least about 90%, at least about 95% or at least about 99% identical to the nucleotide sequence of SEQ ID NO: 1. The disclosure also provide an rAAV comprising a polynucleotide sequence comprising the nucleotide sequence of SEQ ID NO: 1.

The disclosure also provides for rAAV comprising a polynucleotide sequence wherein the polynucleotide sequence comprises i) two self complementary nucleotide sequences, each encoding a gene of interest, wherein the two self complementary nucleotide sequences encoding the gene of interest flank a 5' ITR sequence, ii) two self complementary polyadenylation sequences, wherein the polynucleotide sequence is flanked by two 3' ITR sequences, wherein the two 3' ITR sequences are complementary. For example, the gene of interest is GAD, MTM1, LPL, RPE, REP-1, CNGB3, P1ND4, XLRS, FVIII, FIX, FIX19, AAT, NF-κB, IFN-β, ARSA, NGF, hARSB, Neurturin, AADC, SUMF, SUMF1, OTC, FGF-4, ND4, ARSA, REP1, cytosine deaminase, HGF728, HGF723, hGAA, β-globin gene, Gag, MG1MA3, L523S, METRAP, GDNF, AQP1, PG9DP, HBB, ADA, TCR, CAR, Filgrastim, IL-12, GM-CSF, ICP34.5, PENK, RB94, SST2, DCK. P53, HSC, human sarcoglycan-β (hSCGB), human sarcoglycan γ (hSCGG), human dysferlin, human ANO5, calpain-3 (Cap 3) gene. For example, in the polynucleotide sequence the first nucleotide sequence is the complement sequence of the gene of interest and the second nucleotide sequence encoding the gene of interest is its sense sequence, so that the first nucleotide sequence and the second sequence nucleotide sequence are complementary to each other.

The disclosure also provides for rAAV comprising a polynucleotide, wherein the polynucleotide sequence comprises i) two self complementary nucleotide sequences, each encoding the human alpha-sarcoglycan (hSGCA) protein, such as the amino acid sequence of SEQ ID NO: 3, ii) two self complementary polyadenylation sequences. In some embodiments, the nucleotide sequence encoding the hSGCA protein is at least about 90%, at least about 95% or at least about 99% identical to the nucleotide sequence of SEQ ID NO: 2, or the nucleotide sequence encoding the hSGCA protein comprises the nucleotide sequence of SEQ ID NO: 2. For example, the polyadenylated sequence comprises the nucleotide sequence of SEQ ID NO: 6.

In another aspect, described herein is a recombinant AAV vector comprising a polynucleotide sequence encoding alpha-sarcoglycan. In some embodiments, the polynucleotide sequence encoding alpha-sarcoglycan comprises a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 2 or SEQ ID NO: 7 and encodes protein that retains alpha-sarcoglycan activity. In some embodiments, the polynucleotide sequence encoding alpha-sarcoglycan comprises the nucleotide sequence set forth in SEQ ID NO: 2. In some embodiments, the polynucleotide sequence encoding alpha-sarcoglycan consists of the nucleotide sequence set forth in SEQ ID NO: 2 or SEQ ID NO: 7.

In another aspect, a recombinant AAV vector described herein comprises a polynucleotide sequence encoding alpha-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of SEQ ID NO: 3, and the protein retains alpha-sarcoglycan activity.

In another aspect, described herein is a recombinant AAV vector comprising a polynucleotide sequence encoding functional alpha-sarcoglycan that comprises a nucleotide sequence that hybridizes under stringent conditions to the nucleic acid sequence of SEQ ID NO: 2 or SEQ ID NO: 7, or a complement thereof.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

When ranges are used herein for physical properties, such as molecular weight, concentration, or dosage, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

In addition, any of the provided rAAV comprise a polynucleotide wherein each of the two self complementary nucleotide sequences is operably linked to a muscle-specific control element, wherein the two muscle-specific control elements are self complementary. For example, wherein the muscle-specific control element is human skeletal actin gene element, cardiac actin gene element, myocyte-specific enhancer binding factor (MEF) element, muscle creatine kinase (MCK) promoter, truncated MCK (tMCK) promoter, myosin heavy chain (MHC) promoter, MHCK7 promoter (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypoxia-inducible nuclear factor binding element, steroid-inducible element or glucocorticoid response element (GRE).

In some embodiments, the disclosed rAAV comprises a polynucleotide sequence wherein each of the two complementary nucleotide sequence is operably linked to the muscle-specific control element MCK (tMCK) comprising the nucleotide sequence of SEQ ID NO: 8 or SEQ ID NO: 10.

In an additional embodiment, the disclosed rAAV comprise three inverted terminal repeats (ITRs), wherein one ITR is flanked by the two complementary muscle specific control elements. For example, the ITRs may comprise SEQ ID NO: 5 and/or SEQ ID NO: 9 and/or SEQ ID NO: 12. In a particular example, the ITR that is flanked by the two complementary muscle specific control elements comprises the nucleotide sequence of SEQ ID NO: 8 or 10. In other embodiments, two ITR's comprise the nucleotide sequence of SEQ ID NO: 5 and SEQ ID NO: 12, and one of the ITR's comprises the nucleotide sequence of SEQ ID NO: 9.

The AAV can be any serotype, for example AAV1, AAV2, AAV3, AAV4, AAV5, AAV6, AAV7, AAV8, AAV9, AAV-10, AAV-11, AAV-12, AAV-13, AAVrh.74 or a synthetic AAV serotype. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

The disclosure also provides for compositions comprising any of the disclosed rAAV or any of the disclosed polynucleotides. In some embodiments, the composition further comprises a pharmaceutically acceptable carrier, diluent and/or adjuvant. For example, the composition comprises any of the rAAV of the disclosure, a buffer agent, an ionic strength agent, and a surfactant.

The disclosure provides for methods of treating muscular dystrophy in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure also provides for methods of increasing muscular force and/or muscle mass in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure provides for methods of reducing fibrosis in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure provides for methods of reducing contraction-induced injury in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure provides for methods of treating alpha-sarcoglycanopathy in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

In any of the disclosed methods, the rAAV is administered at a dose of about $1.0\times10^{12}$ vg/kg to about $5.0\times10^{15}$ vg/kg based on a supercoiled DNA or plasmid as the quantitation standard. For example, the rAAV is administered at a dose of about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $2.0\times10^{13}$ vg/kg to about $3.0\times10^{14}$ vg/kg, or about $5\times10^{13}$ vg/kg to about $2\times10^{14}$ vg/kg, or the rAAV is administered at a dose of about $5\times10^{13}$ vg/kg, about $6\times10^{13}$ vg/kg, about $7\times10^{13}$ vg/kg, about $8\times10^{13}$ vg/kg, about $9\times10^{13}$ vg/kg, about $1\times10^{14}$ vg/kg, about $2\times10^{14}$ vg/kg, about $3\times10^{14}$ vg/kg, about $4\times10^{14}$ vg/kg or about $5\times10^{14}$ vg/kg based on a supercoiled DNA or plasmid as the quantitation standard.

In another embodiment, in any of the disclosed methods, the rAAV is administered at a dose about $1.85\times10^{13}$ vg/kg or $7.41\times10^{13}$ vg/kg based on a linearized DNA or plasmid as the quantitation standard. For example, the rAAV is administered at a dose of about $1.0\times10^{13}$ vg/kg to about $8.0\times10^{13}$ vg/kg, about $1.5\times10^{13}$ vg/kg to about $8.0\times10^{13}$ vg/kg, about $1.6\times10^{13}$ vg/kg to about $8.0\times10^{13}$ vg/kg, about $1.8\times10^{13}$ vg/kg to about $8.0\times10^{13}$ vg/kg, about $1.2\times10^{13}$ vg/kg to about $7.5\times10^{13}$ vg/kg, about $1.9\times10^{13}$ vg/kg to about $7.5\times10^{13}$ vg/kg, about $1.4\times10^{13}$ vg/kg to about $7.4\times10^{13}$ vg/kg, about $1.9\times10^{13}$ vg/kg to about $7.5\times10^{13}$ vg/kg, or about $1.8\times10^{13}$ vg/kg to about $8.0\times10^{13}$ vg/kg based on a linearized DNA or plasmid as the quantitation standard.

In addition, in any of the disclosed methods, the systemic route of administration is an intravenous route. For example, in any of the disclosed methods, the rAAV is administered by injection, infusion or implantation. In some embodiments, the rAAV is administered by an intravenous route through a peripheral limb vein.

In any of the disclosed methods, the muscular dystrophy is limb-girdle muscular dystrophy. For example, the muscular dystrophy is limb-girdle muscular dystrophy type 2D (LGMD2D).

In an exemplary embodiment, the methods of treating muscular dystrophy, comprise administering the rAAV to a subject is suffering from limb-girdle muscular dystrophy, and the rAAV is administered by intravenous infusion at a dose of about $5\times10^{13}$ vg/kg to about $2\times10^{14}$ vg/kg based on a supercoiled DNA or plasmid as the quantitation standard, and wherein the rAAV comprises the scAAVrh74.tMCK.hSGCA construct nucleotide sequence of SEQ ID NO: 1.

In exemplary embodiments, the disclosure provides for methods of treating muscular dystrophy in a subject in need thereof, the method comprising the step of administering a rAAV to the subject wherein the subject is suffering from limb-girdle muscular dystrophy, and the rAAV is administered by intravenous infusion at a dose of about $5\times10^{13}$ vg/kg to about $2\times10^{14}$ vg/kg based on a supercoiled DNA or plasmid as the quantitation standard, and wherein the rAAV comprises the scAAVrh74.tMCK.hSGCA construct nucleotide sequence of SEQ ID NO: 1. For example, in these methods, the level of alpha-sarcoglycan gene expression in a cell of the subject is increased after administration of the rAAV as compared to the level of alpha-sarcoglycan gene expression before administration of the rAAV.

In any of the disclosed methods, the level of alpha-sarcoglycan gene expression in a cell of the subject is increased after administration of the rAAV as compared to the level of alpha-sarcoglycan gene expression before administration of the rAAV; and/or wherein the serum CK level in the subject is decreased after administration of the rAAV as compared to serum CK level before administration of the rAAV; and/or wherein the locomotor activity and specific-force generation are increased; wherein fibrosis is reduced; wherein the resistance to contraction-induced injury in tibialis anterior muscle is increased; and/or wherein the number of alpha-sarcoglycan positive fibers in the muscle tissue of the subject is increased after administration of the rAAV as compared to the number of alpha-sarcoglycan positive fibers before administration of the rAAV; or wherein fibrosis is reduced in the subject after administration of the rAAV as compared to before administration of the rAAV; and/or wherein fibrosis is reduced in the subject after administration of the rAAV as compared to before administration of the rAAV; and/or wherein the specific force, the fiber diameter size, and/or the eccentric contraction in the muscle of the subject are increased after administration of the rAAV as compared to before administration of the rAAV.

In some embodiments, the the alpha-sarcoglycan gene expression is detected by measuring the alpha-sarcoglycan protein level by Western blot, and/or immunohistochemistry.

In another aspect, the disclosure provides for methods of expressing alpha-sarcoglycan gene in a cell comprising administering to a subject any of the disclosed rAAV. For example, the disclosure provides for method of expressing the alpha-sarcoglycan gene in a cell comprising administering to a subject the scAAVrh74.tMCK.hSGCA construct nucleotide sequence of SEQ ID NO: 1. In addition, in any of the methods, the expression of the alpha-sarcoglycan gene in the cell of the subject is detected by measuring the alpha-sarcoglycan protein level on a Western blot in muscle biopsies. Alternatively, in any of the methods, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for methods of decreasing serum CK level in a subject in need thereof, the method comprising administering to the subject any of the disclosed rAAV. For example, the disclosure provides for methods of decreasing a serum CK level in a subject in need thereof, the method comprising administering to the subject the scAAVrh74.tMCK.hSGCA construct nucleotide sequence of SEQ ID NO: 1.

In another aspect, the disclosure provide for methods of increasing alpha-sarcoglycan positive fibers in a muscle tissue of a subject comprising administering to the subject any of the disclosed rAAV. For example, the disclosure provides for methods of increasing alpha-sarcoglycan positive fibers in a muscle tissue of a subject in a need thereof, the method comprising administering to the subject the scAAVrh74.tMCK.hSGCA construct nucleotide sequence of SEQ ID NO: 1.

The disclosure also provides for methods of increasing the expression of alpha-sarcoglycan in a subject in need thereof comprising administering to the subject any of the disclosed rAAV. For example, the disclosure provides for methods of increasing the expression of alpha-sarcoglycan in a subject in need thereof, the method comprising administering to the subject the scAAVrh74.tMCK.hSGCA construct nucleotide sequence of SEQ ID NO: 1. In addition, in any of the disclosed methods, the expression of the alpha-sarcoglycan gene in the cell of the subject is detected by measuring the alpha-sarcoglycan protein level on a Western blot in muscle biopsies. Alternatively, in any of the methods, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for compositions for treating muscular dystrophy in a subject in need thereof, wherein the composition comprises any of the rAAV disclosed herein, wherein the composition is formulated for administration by a systemic route. In particular, in any of the compositions, the rAAV is AAVrh74.tMCK.hSCGA.

The disclosure also provides for compositions for increasing muscular force and/or muscle mass in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure provides for compositions for reducing fibrosis in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure provides for compositions for reducing contraction-induced injury in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

The disclosure provides for compositions of treating alpha-sarcoglycanopathy in a subject in need thereof comprising the step of administering any of the rAAV disclosed herein, wherein the rAAV is administered by a systemic route. In particular, in any of the disclosed methods, the rAAV is AAVrh74.tMCK.hSCGA, wherein the rAAV is administered using a systemic route of administration.

Any of the disclosed compositions comprise rAAV at a dose of about $1.0\times10^{12}$ vg/kg to about $5.0\times10^{15}$ vg/kg based on a supercoiled DNA or plasmid as the quantitation standard. For example, the rAAV is at a dose of about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $2.0\times10^{13}$ vg/kg to about $3.0\times10^{14}$ vg/kg, or about $5\times10^{13}$ vg/kg to about $2\times10^{14}$ vg/kg, or the rAAV is at a dose of about $5\times10^{13}$ vg/kg, about $6\times10^{13}$ vg/kg, about $7\times10^{13}$ vg/kg, about $8\times10^{13}$ vg/kg, about $9\times10^{13}$ vg/kg, about $1\times10^{14}$ vg/kg, about $2\times10^{14}$ vg/kg, about $3\times10^{14}$ vg/kg, about $4\times10^{14}$ vg/kg or about $5\times10^{14}$ vg/kg based on a supercoiled DNA or plasmid as the quantitation standard.

In another embodiment, in any of the disclosed compositions, the rAAV is administered at a dose about $1.85\times10^{13}$ vg/kg or about $7.41\times10^{13}$ vg/kg based on a linearized DNA or plasmid as the quantitation standard. For example, the rAAV is administered at a dose of about $1.0\times10^{13}$ vg/kg to about $8.0\times10^{13}$ vg/kg, about $1.5\times10^{13}$ vg/kg to about $8.0\times10^{13}$ vg/kg, about $1.6\times10^{13}$ vg/kg to about $8.0\times10^{13}$ vg/kg, about $1.8\times10^{13}$ vg/kg to about $8.0\times10^{13}$ vg/kg, about $1.2\times10^{13}$ vg/kg to about $7.5\times10^{13}$ vg/kg, about $1.9\times10^{13}$ vg/kg to about $7.5\times10^{13}$ vg/kg, about $1.4\times10^{13}$ vg/kg to about $7.4\times10^{13}$ vg/kg, about $1.9\times10^{13}$ vg/kg to about $7.5\times10^{13}$ vg/kg, or about $1.8\times10^{13}$ vg/kg to about $8.0\times10^{13}$ vg/kg based on a linearized DNA or plasmid as the quantitation standard.

In addition, any of the disclosed compositions are formulated for administration by an intravenous route, such as compositions formulated for administration by injection, infusion or implantation. In some embodiments, the disclosed compositions are formulated for administration by an intravenous route through a peripheral limb vein.

Any of the disclosed compositions are for the treatment for limb-girdle muscular dystrophy, such as limb-girdle muscular dystrophy type 2D (LGMD2D).

In an exemplary embodiment, the disclosure provides for compositions for treating a subject suffering from limb-girdle muscular dystrophy, wherein the composition comprises a dose of rAAV at about $5\times10^{13}$ vg/kg to about $2\times10^{14}$ vg/kg based on a supercoiled DNA or plasmid as the quantitation standard, and wherein the composition is formulated for administration by intravenous infusion, and wherein the rAAV comprises the scAAVrh74.tMCK.hSGCA construct nucleotide sequence of SEQ ID NO: 1.

In addition, the disclosure provides for compositions for treating limb-girdle muscular dystrophy in a subject in need thereof, wherein the composition comprises a dose of rAAV of about $5\times10^{13}$ vg/kg to about $2\times10^{14}$ vg/kg based on a supercoiled DNA or plasmid as the quantitation standard, and the composition is formulated for administration by intravenous infusion and wherein the rAAV comprises the scAAVrh74.tMCK.hSGCA construct nucleotide sequence of SEQ ID NO: 1. For example, administration of the composition increases the level of alpha-sarcoglycan gene expression in a cell of the subject as compared to the level of alpha-sarcoglycan gene expression before administration of the composition.

In addition, administration of any of the disclosed compositions increases the level of alpha-sarcoglycan gene expression in a cell of the subject as compared to the level of alpha-sarcoglycan gene expression before administration of the composition; and/or wherein administration of the disclosed composition decreased the serum CK level in the subject as compared to serum CK level before administration of the composition; and/or wherein the locomotor activity and specific-force generation are increased; wherein fibrosis is reduced; wherein the resistance to contraction-induced injury in tibialis anterior muscle is increased; and/or wherein administration of the composition increases the number of alpha-sarcoglycan positive fibers in the muscle tissue of the subject as compared to the number of alpha-sarcoglycan positive fibers before administration of the composition; and/or wherein administration of composition reduced fibrosis in the subject as compared to before administration of the rAAV; and/or wherein the composition reduced fibrosis as compared to before administration of the composition; or wherein administration of the composition increased the specific force, the fiber diameter size, and/or the eccentric contraction in the muscle of the subject as compared to before administration of the composition. In some embodiments, the alpha-sarcoglycan gene expression is detected by measuring the alpha-sarcoglycan protein level by Western blot, and/or immunohistochemistry.

In another aspect, the disclosure provides for compositions for expressing alpha-sarcoglycan gene in a cell, wherein composition comprises any of the disclosed rAAV. For example, the disclosure provides compositions for expressing alpha-sarcoglycan gene in a cell comprising the scAAVrh74.tMCK.hSGCA construct nucleotide sequence of SEQ ID NO: 1. In addition, in any of the compositions, the expression of the alpha-sarcoglycan gene in the cell of the subject is detected by measuring the alpha-sarcoglycan protein level on a Western blot in muscle biopsies. Alternatively, in any of the methods, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for compositions for decreasing a serum CK level in a subject in need thereof, the composition comprising any of the disclosed rAAV. For example, the disclosure provides for compositions for decreasing a serum CK level in a subject in need thereof, the composition comprises the scAAVrh74.tMCK.hSGCA construct nucleotide sequence of SEQ ID NO: 1.

In another aspect, the disclosure provides for composition for increasing alpha-sarcoglycan positive fibers in a muscle tissue of a subject, wherein the composition comprises any of the disclosed rAAV. For example, the disclosure provides for compositions for increasing alpha-sarcoglycan positive fibers in a muscle tissue of a subject, wherein the composition comprises the scAAVrh74.tMCK.hSGCA construct nucleotide sequence of SEQ ID NO: 1.

The disclosure also provides for composition for increasing the expression of alpha-sarcoglycan in a subject in need thereof, wherein the composition comprises any of the disclosed rAAV. For example, the disclosure provides compositions for increasing the expression of alpha-sarcoglycan in a subject in need thereof, wherein the composition comprises the scAAVrh74.tMCK.hSGCA construct nucleotide sequence of SEQ ID NO: 1. In addition, after administration of the any of the disclosed compositions, the expression of the alpha-sarcoglycan gene in the cell of the subject is detected by measuring the alpha-sarcoglycan protein level on a Western blot in muscle biopsies. Alternatively, after administration of the any of the disclosed compositions, the expression of the alpha-sarcoglycan gene in the cell is detected by measuring the alpha-sarcoglycan protein level by immunohistochemistry in muscle biopsies. In other embodiments, after administration of the any of the disclosed compositions, the expression of the alpha-sarcoglycan gene is measured in the subject by detecting the number of vector genome per microgram of genomic DNA.

The disclosure provides for use of any of the disclosed rAAV for the preparation of a medicament for the treating muscular dystrophy in a subject in need thereof, wherein the medicament is formulated for administration by a systemic route. In particular, the disclosure provides for use of AAVrh74.tMCK.hSCGA for the preparation of a medicament for treating muscular dystrophy, wherein the medicament is formulated for administration by a systemic route of administration.

The disclosure also provides for use of any of the disclosed rAAV for the preparation of a medicament for increasing muscular force and/or muscle mass in a subject in need thereof. In particular, the disclosure provides for a use wherein the rAAV is AAVrh74.tMCK.hSCGA, wherein the rAAV is administered using a systemic route of administration.

The disclosure also provides for use of any of the disclosed rAAV for the preparation of a medicament for reducing fibrosis in a subject in need thereof. In particular, the disclosure provides for a use wherein the rAAV is AAVrh74.tMCK.hSCGA, wherein the rAAV is administered using a systemic route of administration.

The disclosure also provides for use of any of the disclosed rAAV for the preparation of a medicament for reducing contraction-induced injury in a subject in need thereof. In particular, the disclosure provides for a use wherein the rAAV is AAVrh74.tMCK.hSCGA, wherein the rAAV is administered using a systemic route of administration.

The disclosure also provides for use of any of the disclosed rAAV for the preparation of a medicament for treating alpha-sarcoglycanopathy in a subject in need thereof. In particular, the disclosure provides for a use wherein the rAAV is AAVrh74.tMCK.hSCGA, wherein the rAAV is administered using a systemic route of administration.

In any of the disclosed uses, the medicament comprises rAAV at a dose of about $1.0\times10^{12}$ vg/kg to about $5.0\times10^{15}$ vg/kg based on a supercoiled DNA or plasmid as the quantitation standard. For example, the rAAV is at a dose of about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $2.0\times10^{13}$ vg/kg to about $3.0\times10^{14}$ vg/kg, or about $5\times10^{13}$ vg/kg to about $2\times10^{14}$ vg/kg, or the rAAV is at a dose of about $5\times10^{13}$ vg/kg, about $6\times10^{13}$ vg/kg, about $7\times10^{13}$ vg/kg, about $8\times10^{13}$ vg/kg, about $9\times10^{13}$ vg/kg, about $1\times10^{14}$ vg/kg, about $2\times10^{14}$ vg/kg, about $3\times10^{14}$ vg/kg, about $4\times10^{14}$ vg/kg or about $5\times10^{14}$ vg/kg based on a supercoiled DNA or plasmid as the quantitation standard.

In another embodiment, in any of the disclosed uses, the medicament comprises rAAV at a dose about $1.85\times10^{13}$ vg/kg or $7.41\times10^{13}$ vg/kg based on a linearized DNA or plasmid as the quantitation standard. For example, the medicament comprises rAAV at a dose of about $1.0\times10^{13}$ vg/kg to about $8.0\times10^{13}$ vg/kg, about $1.5\times10^{13}$ vg/kg to about $8.0\times10^{13}$ vg/kg, about $1.6\times10^{13}$ vg/kg to about $8.0\times10^{13}$ vg/kg, about $1.8\times10^{13}$ vg/kg to about $8.0\times10^{13}$ vg/kg, about $1.2\times10^{13}$ vg/kg to about $7.5\times10^{13}$ vg/kg, about $1.9\times10^{13}$ vg/kg to about $7.5\times10^{13}$ vg/kg, about $1.4\times10^{13}$ vg/kg to about $7.4\times10^{13}$ vg/kg, about $1.9\times10^{13}$ vg/kg to about $7.5\times10^{13}$ vg/kg, or about $1.8\times10^{13}$ vg/kg to about $8.0\times10^{13}$ vg/kg based on a linearized DNA or plasmid as the quantitation standard.

In addition, in any of the disclosed uses, the medicament is formulated for administration by an intravenous route. For example, in any of the disclosed uses, the medicament is formulated for administration by injection, infusion or implantation. In some embodiments, the medicament is formulated for administration by an intravenous route through a peripheral limb vein.

In any of the disclosed uses, the medicament is for the treatment of limb-girdle muscular dystrophy, such as limb-girdle muscular dystrophy type 2D (LGMD2D).

In an exemplary embodiment, the disclosure provides for use of a rAAV for the preparation of a medicament for treating limb-girdle muscular dystrophy, wherein the medicament is formulated for administration by intravenous infusion and the rAAV is at a dose of about $5\times10^{13}$ vg/kg to about $2\times10^{14}$ vg/kg based on a supercoiled DNA or plasmid as the quantitation standard, and wherein the rAAV comprises the scAAVrh74.tMCK.hSGCA construct nucleotide sequence of SEQ ID NO: 1. For example, administration of the medicament to a subject in need results in an increase in alpha-sarcoglycan gene expression in a cell of the subject as compared to the level of alpha-sarcoglycan gene expression before administration of the rAAV.

In any of the disclose uses, administration of the medicament to a subject in need results in an increase in the level of alpha-sarcoglycan gene expression in a cell of the subject as compared to the level of alpha-sarcoglycan gene expression before administration of the medicament; and/or administration of the medicament to a subject results in decrease in the the serum CK level in the subject as compared to serum CK level before administration of the medicament; and/or wherein the locomotor activity and specific-force generation are increased; wherein fibrosis is reduced; wherein the resistance to contraction-induced injury in tibialis anterior muscle is increased; and/or administration of the medicament to the subject results in an increase in the number of alpha-sarcoglycan positive fibers in the muscle tissue of the subject is increased as compared to the number of alpha-sarcoglycan positive fibers before administration of the medicament, and/or administration of the medicament to the subject in need results in reduced fibrosis in the subject as compared to before administration of the medicament;

and/or administration of the medicament results in an increase in the specific force, the fiber diameter size, and/or the eccentric contraction in the muscle of the subject as compared to before administration of the medicament. In some embodiments, the alpha-sarcoglycan gene expression is detected by measuring the alpha-sarcoglycan protein level by Western blot, and/or immunohistochemistry.

In another aspect, the disclosure provides for use of any of the disclosed rAAV for the preparation of a medicament for expressing alpha-sarcoglycan gene in a cell in a subject in need. For example, the disclosure provides for use of scAAVrh74.tMCK.hSGCA construct for the preparation of a medicament for expressing alpha-sarcoglycan gene in a cell in a subject in need, wherein the scAAVrh74.tMCK.hSGCA construct comprises a nucleotide sequence of SEQ ID NO: 1. In addition, in any of the uses, the expression of the alpha-sarcoglycan gene in the cell of the subject is detected by measuring the alpha-sarcoglycan protein level on a Western blot in muscle biopsies. Alternatively, in any of the uses, the expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

The disclosure provides for use of any of the disclosed rAAV for the preparation of medicament for decreasing a serum CK level in a subject in need thereof. For example, the disclosure provides for use of scAAVrh74.tMCK.hSGCA construct for the preparation of a medicament for decreasing a serum CK level in a subject in need thereof, wherein scAAVrh74.tMCK.hSGCA construct comprises the nucleotide sequence of SEQ ID NO: 1.

In another aspect, the disclosure provides for use of any of the disclosed rAAV for the preparation of a medicament for increasing alpha-sarcoglycan positive fibers in a muscle tissue of a subject. For example, the disclosure provides for use of scAAVrh74.tMCK.hSGCA construct for the preparation of a medicament for increasing alpha-sarcoglycan positive fibers in a muscle tissue of a subject, wherein scAAVrh74.tMCK.hSGCA construct comprises the nucleotide sequence of SEQ ID NO: 1.

The disclosure also provides for use any of the disclosed rAAV for the preparation of a medicament for increasing the expression of alpha-sarcoglycan in a subject in need thereof. For example, the disclosure provides for use of scAAVrh74.tMCK.hSGCA construct for the preparation of a medicament for increasing the expression of alpha-sarcoglycan in a subject in need thereof, wherein the scAAVrh74.tMCK.hSGCA construct comprises the nucleotide sequence of SEQ ID NO: 1. In addition, in any of the disclosed uses, the expression of the alpha-sarcoglycan gene in the cell of the subject is detected by measuring the alpha-sarcoglycan protein level on a Western blot in muscle biopsies. Alternatively, in any of the disclosed uses, expression of the alpha-sarcoglycan gene in the cell is detected by measuring the alpha-sarcoglycan protein level by immunohistochemistry in muscle biopsies. In other embodiments, the expression of the alpha-sarcoglycan gene is measured in the subject by detecting the number of vector genome per microgram of genomic DNA.

In any of the disclosed methods, compositions or uses, the subject is a human subject that is 4 to 15 years of age, or a human subject that is 25 to 55 years of age or a human subject that is over 50 years of age.

In any of the disclosed methods, compositions or uses, the subject is a pediatric subject, an adolescent subject or a young adult subject. Alternatively, the subject is a middle aged adult or elderly subject.

For example, in any of the disclosed methods, compositions or uses, the subject is a human subject that is 4-15 years of age, has a confirmed alpha-sarcoglycan (SGCA) mutation in both alleles, was negative for AAVrh74 antibodies and/or had >40% or normal 100 meter walk test.

In another aspect, provided is a method of generating the rAAV disclosed herein, comprising transferring a plasmid to a cell, wherein the plasmid comprises a nucleotide sequence that is at least about 90%, at least about 95%, or at least about 99% identical to SEQ ID NO: 1. In particular, the plasmid comprises a nucleotide sequence of SEQ ID NO: 1.

In any of the disclosed methods of generating a rAAV, the method further comprises transferring a packaging plasmid and/or a helper virus to the host cell. In addition, in any of the disclosed methods of generating a rAAV, a packaging cell comprises a stably integrated AAV cap gene and/or comprises a packaging cell comprises a stably integrated AAV rep gene.

In another aspect, the disclosure provisdes for host cells comprising an AAV vector plasmid that comprises a nucleotide sequence that is at least 90%, 91%, 92%, 93%, 94%, 95%, 96%, 97%, 98%, or 99% identical to SEQ ID NO: 1. For example, the host cell comprises an AAV vector plasmid that comprises a nucleotide sequence of SEQ ID NO: 1.

Methods of producing a recombinant AAV vector particle comprising culturing a cell that is transferred with a plasmid described herein and recovering recombinant AAV particles from the supernatant of the transfected cells are also provided. Viral particles comprising any of the recombinant AAV vectors described herein are also contemplated. In one embodiment, the method of generating the rAAV comprises transferring an AAV vector plasmid to a host cell. In another embodiment, the plasmid comprises a nucleotide sequence that is at least about 90%, at least about 95%, or at least about 99% identical to SEQ ID NO: 1. In another aspect, the disclosure provides a cell comprising an AAV vector plasmid that comprises a nucleotide sequence of SEQ ID NO: 1. The cell described herein may be an insect cell, e.g., a *Drosophila* cell (e.g., an S2 cell or Kc cell), a silkworm cell (e.g., a Bme21 cell), or a mosquito cell (e.g., a C6/36 cell); or a mammalian cell (preferably a human cell, e.g., a human primary cell or an established cell line). In one embodiment, the mammalian cell is a 293 cell, a COS cell, a Hela cells, or a KB cell.

In another embodiment, the plasmid comprises a nucleotide sequence that is at least about 90%, at least about 95%, or at least about 99% identical to SEQ ID NO: 1. In some embodiments, the vector plasmid comprises a nucleotide sequence of any one of SEQ ID NO: 1. In some embodiments, the AAV vector plasmid is stably expressed in the host cell. The host cell stably harboring the AAV vector plasmid can be used to generate rAAV.

The method of producing recombinant AAV vector particles provided herein may further comprise a step of transferring a packaging plasmid and/or a helper virus to the host cell. For example, the methods further comprise a step wherein the packaging cell comprises a stably integrated AAV cap gene and/or wherein the packaging cell comprises a stably integrated AAV rep gene. The disclosure also provides for a cell comprising a plasmid that comprises a nucleotide sequence that is at least about 90%, at least about 95%, or at least about 99% identical to SEQ ID NO: 1 or a plasmid that comprises a nucleotide sequence of SEQ ID NO: 1. Also provided is a cell comprising a nucleotide sequence of SEQ ID NO: 1.

Methods of reducing fibrosis in a subject in need thereof is also provided. In this regard, the method comprises administering a therapeutically effective amount of an AAV vector described herein (or composition comprising an rAAV vector described herein) to the mammalian subject. In some embodiments, the subject suffers from muscular dystrophy. In some embodiments, administration of an rAAV vector described herein (or composition comprising an rAAV vector described herein) reduces fibrosis in skeletal muscle or in cardiac muscle of the subject.

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 21 muscular dystrophy, limb-girdle type 21 muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject is suffering from limb-girdle muscular dystrophy type 2D (LGMD2D).

The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g. collagen 1, collagen 2 or collagen 3, and fibronectin.

In another aspect, described herein is a method of increasing muscular force and/or muscle mass in a mammalian subject comprising administering a therapeutically effective amount of an AAV vector described herein (or composition comprising an AAV vector described herein) to the mammalian subject. In one embodiment, the subject is a human.

In any of the provided formulations or compositions, the buffer agent comprises one or more of tris, tricine, Bis-tricine, HEPES, MOPS, TES, TAPS, PIPES, and CAPS. For example, the buffer agent comprises the tris with pH 8.0 at concentration of about 5 mM to about 40 mM or the buffer agent comprises the tris with pH 8.0 at about 20 mM.

In any of the provided formulations or compositions, the ionic strength agent comprises one or more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. For example, the ionic strength agent comprises $MgCl_2$ at a concentration of about 0.2 mM to about 4 mM or the ionic strength agent comprises NaCl at a concentration of about 50 mM to about 500 mM, or the ionic strength agent comprises $MgCl_2$ at a concentration of about 0.2 mM to about 4 mM and NaCl at a concentration of about 50 mM to about 500 mM, or the ionic strength agent comprises $MgCl_2$ at a concentration of about 1 mM and NaCl at a concentration of about 200 mM.

In any of the provided formulations or compositions, the surfactant comprises one or more of a sulfonate, a sulfate, a phosphonate, a phosphate, a Poloxamer, and a cationic surfactant. For example, the Poloxamer comprises one or more of Poloxamer 124, Poloxamer 181, Poloxamer 184, Poloxamer 188, Poloxamer 237, Poloxamer 331, Poloxamer 338, and Poloxamer 407. The poloxamer may be at a concentration of about 0.00001% to about 1%. An exemplary surfactant is Poloxamer 188 at a concentration of about 0.001%.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

BRIEF DESCRIPTION OF THE FIGURES

FIGS. 2A-2D provide an annotated nucleotide sequence of scAAVrh74.tMCK.hSGCA.

DETAILED DESCRIPTION

Figure 1:
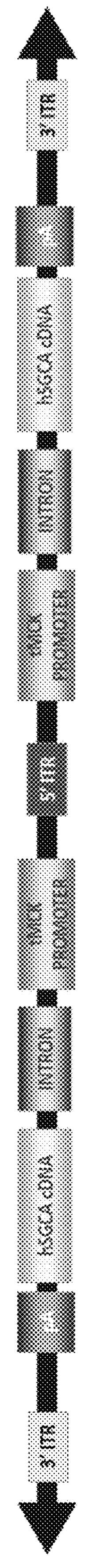
FIG. 1 provides a schematic of scAAVrh74.tMCK.hSGCA therapeutic alpha-sarcoglycan transgene cassette. Self-complementary AAV vector containing the codon-optimized human alpha-sarcoglycan gene (hSGCA). A muscle specific tMCK promoter drives expression. The cassette also contains a chimeric intron to augment processing and polyadenylation signal for stability.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijssen, ed.); Fundamental Virology, 2nd Edition, vol. I & II (B. N. Fields and D. M. Knipe, eds.); Freshney Culture of Animal Cells, A Manual of Basic Technique (Wiley-Liss, Third Edition); and Ausubel et al. (1991) Current Protocols in Molecular Biology (Wiley Interscience, N.Y.).

Definitions

As used herein, the singular forms "a," "an," and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. Reference to "a recombinant AAV" includes a mixture of two or more rAAV virions, and the like. All technical and scientific terms used herein have the same meaning as commonly understood to one of ordinary skill in the art to which this invention belongs unless clearly indicated otherwise.

The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the statistical experimental error (standard deviation of error) for the device or method being employed to determine the value.

The term "vector" is meant to be any genetic element, such as a plasmid, phage, transposon, cosmid, chromosome, virus, virion, etc., which is capable of replication when associated with the proper control elements and which can transfer gene sequences between cells. In one embodiment, the vector is a viral vector.

As used herein, the term "AAV" is a standard abbreviation for adeno-associated virus. Adeno-associated virus is a single-stranded DNA parvovirus that grows only in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products. In one embodiment, the AAV vector is a vector derived from an adeno-associated virus serotype, including without limitation, AAV-1, AAV-2, AAV-3, AAV-4, AAV-5, AAV-6, AAV-7, AAV-8, AAV-9, AAV-10, AAV-11, AAV-12, AAV-13, AAV rh10, and AAVrh.74. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, as long as the sequences provide for functional rescue, replication and packaging.

The term "AAV helper functions" refer to AAV-derived coding sequences that can be expressed to provide AAV gene products that, in turn, function in trans for productive AAV replication. Thus, AAV helper functions comprise the major AAV open reading frames (ORFs), reps and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

By "recombinant virus" is meant a virus that has been genetically altered, e.g., by the addition or insertion of a heterologous nucleic acid sequence into the viral particle.

An "AAV virion" or "AAV viral particle" or "AAV vector particle" refers to a viral particle composed of at least one AAV capsid protein and an encapsidated polynucleotide AAV vector. The AAV virion, in one embodiment, comprises a heterologous polynucleotide (i.e. a polynucleotide other than a wild-type AAV genome such as a transgene to be delivered to a mammalian cell). Production of AAV viral particles, in some embodiments, includes production of AAV vector, as such a vector is contained within an AAV vector particle.

AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

For example, a wild-type (wt) AAV virus particle comprising a linear, single-stranded AAV nucleic acid genome associated with an AAV capsid protein coat. The AAV virion can be either a single-stranded (ss) AAV or self-complementary (SC) AAV. In one embodiment, a single-stranded AAV nucleic acid molecules of either complementary sense, e.g., "sense" or "antisense" strands, can be packaged into a AAV virion and both strands are equally infectious.

The term "recombinant AAV," or "rAAV" is defined herein as an infectious, replication-defective virus composed of an AAV protein shell, encapsidating a heterologous nucleotide sequence of interest which is flanked on both sides by AAV ITRs. An rAAV, in one embodiment, is produced in a suitable host cell which has an AAV vector, AAV helper functions and accessory functions introduced therein. In this manner, the host cell is capable of encoding AAV polypeptides that are required for packaging the AAV vector (containing a recombinant nucleotide sequence of interest) into infectious recombinant virion particles for subsequent gene delivery.

The term "transfection" refers to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect. cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "transduction" is used to refer to the administration/delivery of a polynucleotide of interest (e.g., a polynucleotide sequence encoding β-sarcoglycan) to a recipient cell either in vivo or in vitro, via a replication-deficient rAAV described resulting in expression of β-sarcoglycan by the recipient cell.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The nucleic acids include base analogues of DNA and RNA including, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters." In one embodiment, the promoter is a muscle-specific promoter, which includes but is not limited to, a human skeletal actin gene element, a cardiac actin gene element, a desmin promoter, a skeletal alpha-actin (ASKA) promoter, a troponin I (TNNI2) promoter, a myocyte-specific enhancer binding factor (mef) binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor (HIF)-response element (HRE), a steroid-inducible element, and a glucocorticoid response element (GRE). In another embodiment, the promoter is an MCK promoter, a tMCK promoter, or an MHCK7 promoter.

The term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A promoter "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA, at least one multiple cloning site, and a "mammalian" origin of replication (e.g., a SV40 or adenovirus origin of replication).

By "isolated" when referring to a nucleotide sequence, is meant that the indicated molecule is present in the substantial absence of other biological macromolecules such as other nucleotide sequences, chromatin material, etc. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5' relative to another sequence, it is to be understood that it is the position of the sequences in the "sense" or "coding" strand of a DNA molecule that is being referred to as is conventional in the art.

The terms "sequence identity", "percent sequence identity", or "percent identical" in the context of nucleic acid or amino acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. The percent identity of the sequences can be determined by techniques known in the art. For example, homology can be determined by a direct comparison of the sequence information between two polypeptide molecules by aligning the sequence information and using readily available computer programs such as ALIGN, ClustalW2 and BLAST. In one embodiment, when BLAST is used as the alignment tool, the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

The term "subject" refers to any member of the animal kingdom, which includes, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. In some embodiments, the subject is a human ranging in age from birth to 2 years, from 1 to 10 years, or ranging from 4 to 15 years, or ranging from 10 to 19 years, or from 20 to 40 years of age, or from 15 to 29 years of age or from 25-55 years, or ranging from 40 to 60 years, or over 50 years or over 60 years or over 65 years or over 70 years.

AAV

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., J Virol, 45: 555-564 (1983) as corrected by Ruffing et al., J Gen Virol, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). Cloning of the AAVrh.74 serotype is described in Rodino-Klapac, et al. Journal of translational medicine 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° C. to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2: 619-623 (2000) and Chao et al., Mol Ther, 4: 217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics.

Recombinant AAV genomes of the disclosure comprise nucleic acid molecule of the disclosure and one or more AAV ITRs flanking a nucleic acid molecule. AAV DNA in the rAAV genomes may be from any AAV serotype for which a recombinant virus can be derived including, but not limited to, AAV serotypes AAVrh.74, AAV-1, AAV-2, AAV-3, AAV-4, AAV-5, AAV-6, AAV-7, AAV-8, AAV-9, AAV-10, AAV-11, AAV-12, AAV-13, AAVrh. 10 and AAVrh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote muscle-specific expression, AAVrh.74 can be used.

DNA plasmids of the disclosure comprise rAAV genomes of the disclosure. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12, AAVrh. 10, AAVrh.74 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79: 2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial, and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mo1. Cell. Biol. 5:3251 (1985); Mclaughlin et al., J. Virol., 62:1963 (1988); and Lebkowski et al., Mol. Cell. Biol., 7:349 (1988). Samulski et al., J. Virol., 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. Vaccine 13:1244-1250 (1995); Paul et al. Human Gene Therapy 4:609-615 (1993); Clark et al. Gene Therapy 3:1124-1132 (1996); U.S. Pat. Nos. 5,786,211; 5,871,982; and 6,258,595. The foregoing documents are hereby incorporated by reference in their entirety herein, with particular emphasis on those sections of the documents relating to rAAV production.

The disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the disclosure comprise a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the disclosure are set out in International Patent Application No. PCT/US2012/047999 (WO 2013/016352) incorporated by reference herein in its entirety.

In an exemplary embodiment, the recombinant AAV vector of the disclosure is produced by the triple transfection method (Xiao et al., J Virol 72, 2224-2232 (1998) using the AAV vector plasmids scAAV.tMCK.hSCGA, pNLRep2-Caprh74 and pHelp, rAAV contains the hSCGA gene expression cassette flanked by AAV2 inverted terminal repeat sequences (ITR). It is this sequence that is encapsidated into AAVrh.74 virions. The plasmid contains the hSCGA sequence and the MHCK7 enhancer and core promoter elements of the muscle specific promoter to drive gene expression. The expression cassette also contains an SV40 intron (SD/SA) to promote high-level gene expression and the bovine growth hormone polyadenylation signal is used for efficient transcription termination.

The pNLREP2-Caprh74 is an AAV helper plasmid that encodes the 4 wild-type AAV2 rep proteins and the 3 wild-type AAV VP capsid proteins from serotype rh74.

The pHELP adenovirus helper plasmid is 11,635 bp and was obtained from Applied Viromics. The plasmid contains the regions of adenovirus genome that are important for AAV replication, namely E2A, E4ORF6, and VA RNA (the adenovirus E1 functions are provided by the 293 cells). The adenovirus sequences present in this plasmid only represents ~40% of the adenovirus genome, and does not contain the cis elements critical for replication such as the adenovirus terminal repeats. Therefore, no infectious adenovirus is expected to be generated from such a production system.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10 (6): 1031-1039 (1999); Schenpp and Clark, Methods Mol. Med., 69 427-443 (2002); U.S. Pat. No. 6,566,118 and WO 98/09657.

In another embodiment, the disclosure contemplates compositions comprising rAAV of the present disclosure. Compositions of the disclosure comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed and include buffers and surfactants such as pluronics.

Titers of rAAV to be administered in methods of the disclosure will vary depending, for example, on the particular rAAV, the mode of administration, the treatment goal, the individual, and the cell type(s) being targeted, and may be determined by methods standard in the art. Titers of rAAV may range from about 1×106, about 1×107, about 1×108, about 1×109, about 1×1010, about 1×1011, about 1×1012, about 1×1013 to about 1×1014 or more DNase resistant particles (DRP) per ml. Dosages may also be expressed in units of viral genomes (vg). One exemplary method of determining encapsilated vector genome titer uses quantitative PCR such as the methods described in (Pozsgai et al., Mol. Ther. 25(4): 855-869, 2017). Unless stated otherwise, the dosages described herein correspond to a dose as determined by the supercoiled DNA standard.

Methods of transducing a target cell with rAAV, in vivo or in vitro, are contemplated by the disclosure. The in vivo methods comprise the step of administering an effective dose, or effective multiple doses, of a composition comprising a rAAV of the disclosure to an animal (including a human being) in need thereof. If the dose is administered prior to development of a disorder/disease, the administration is prophylactic. If the dose is administered after the development of a disorder/disease, the administration is therapeutic. In embodiments of the disclosure, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the disclosure is muscular dystrophy, e.g. limb girdle muscular dystrophy or Duchenne muscular dystrophy.

Combination therapies are also contemplated by the disclosure. Combination as used herein includes both simultaneous treatment and sequential treatments. Combinations of methods of the disclosure with standard medical treatments (e.g., corticosteroids) are specifically contemplated, as are combinations with novel therapies.

Administration of an effective dose of the compositions, combination therapies or medicaments may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the disclosure may be chosen and/or matched by those skilled in the art taking into account the infection and/or disease state being treated and the target cells/tissue(s) that are to express the hSCGA protein.

The disclosure provides for local administration and systemic administration of an effective dose of rAAV, medicaments and compositions of the disclosure. For example, systemic administration is administration into the circulatory system so that the entire body is affected. Systemic administration includes enteral administration such as absorption through the gastrointestinal tract and parenteral administration through injection, infusion or implantation.

In particular, actual administration of rAAV of the present disclosure may be accomplished by using any physical method that will transport the rAAV recombinant vector into the target tissue of an animal. Administration according to the disclosure includes, but is not limited to, injection into muscle and injection into the bloodstream. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the disclosure. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the disclosure results in sustained expression of the hSCGA protein. The present disclosure thus provides methods of administering/delivering rAAV which express hSCGA protein to an animal, preferably a human being. These methods include transducing tissues (including, but not limited to, tissues such as muscle, organs such as liver and brain, and glands such as salivary glands) with one or more rAAV of the present disclosure. Transduction may be carried out with gene cassettes comprising tissue specific control elements. For example, one embodiment of the disclosure provides methods of transducing muscle cells and muscle tissues directed by muscle specific control elements, including, but not limited to, those derived from the actin and myosin gene families, such as from the myoD gene family (See Weintraub et al., Science, 251: 761-766 (1991)), the myocyte-specific enhancer binding factor MEF-2 (Cserjesi and Olson, Mol Cell Biol 11: 4854-4862 (1991)), control elements derived from the human skeletal actin gene (Muscat et al., Mol Cell Biol, 7: 4089-4099 (1987)), the cardiac actin gene, muscle creatine kinase sequence elements (See Johnson et al., Mol Cell Biol, 9: 3393-3399 (1989)) and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., Proc Natl Acad Sci USA, 88: 5680-5684 (1991)), steroid-inducible elements and promoters including the glucocorticoid response element (GRE) (See Mader and White, Proc. Natl. Acad. Sci. USA 90: 5603-5607 (1993)), and other control elements.

Muscle tissue is an attractive target for in vivo DNA delivery, because it is not a vital organ and is easy to access. The disclosure contemplates sustained expression of hSCGA from transduced myofibers.

Thus, the disclosure provides methods of administering an effective dose (or doses, administered essentially simultaneously or doses given at intervals) of rAAV that encode hSCGA to a subject in need thereof.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). The titers of rAAV may be determined by the supercoiled plasmid quantitation standard or the linearized plasmid quantitation standard.

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is muscular dystrophy, such as limb-girdle muscular dystrophy. Thus, provided is a method of tranducing a target cell with an rAAV scAAVrh74.tMCK.hSGCA, which comprises a nucleotide sequence of SEQ ID NO: 1.

Combination therapies are also contemplated by the invention. Combination as used herein includes both simultaneous treatment or sequential treatments. Combinations of methods of the invention with standard medical treatments (e.g., steroids, corticosteroids, and/or glucocorticoids including but not limited to one or more of prednisone, prednisolone; and deflazacort) are specifically contemplated, as are combinations with novel therapies. In this regard, the combinations include administering to a subject one or more steroids, corticosteroids, and/or glucocorticoids including but not limited to one or more of prednisone, prednisolone; and deflazacort before administering an rAAV of the inventive methods to the subject, simultaneously with administering the rAAV to the subject, or after administering the rAAV to the subject.

In related embodiments of a combination therapy contemplated by the invention, the glucocorticoid includes, but is not limited to beclomethasone, betamethasone, budesonide, cortisone, dexamethasone, hydrocortisone, methylprednisolone, or triamcinolone.

It is recognized that an antigen specific T-cell response may occur in a subject administered with the rAAV vector. This is an expected response between 2-4 weeks following gene transfer. One possible consequence to such antigen specific T-cell responses is clearance of the transduced cells and loss of transgene expression. To dampen the host immune response to the rAAV based therapy, before the therapy, for example, twenty-four hours prior to the therapy procedure, subjects can be started on approximately 1 mg/kg/day prophylactic prednisone or comparable glucocorticoid by mouth with a maximum dose of 60 mg/day. IV administration of a comparable glucocorticoid at the approximate dose of 1 mg/kg/day would also be allowable if needed. Treatment will continue for approximately one month. A tapering protocol for prednisone or comparable glucocorticoid can be implemented based on individual subjects' immune response to the gene transfer, assessed by ELISpot assay and also by liver function monitoring with GGT.

Provided are methods of treating muscular dystrophy in a human subject in need thereof comprising the step of administering a recombinant adeno-associated virus (rAAV) scAAVrh74.tMCK.hSGCA, wherein the rAAV is administered using at a dose of about $1.0\times10^{12}$ vg/kg to about $5.0\times10^{15}$ vg/kg. For example, in any of the provided methods, the dose of the rAAV administered is between about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $5\times10^{13}$ vg/kg to about $2\times10^{14}$ vg/kg, or about $2.0\times10^{13}$ vg/kg to about $3.0\times10^{14}$ vg/kg. In another embodiment, the dose is about $5.0\times10^{13}$ vg/kg, $1.0\times10^{14}$ vg/kg, or $2.0\times10^{14}$ vg/kg. In one embodiment, the rAAV is administered by a systemic route, which comprises an intravenous route. In another embodiment, the rAAV is administered intravenously at a dose of about $5.0\times10^{13}$ vg/kg, $1.0\times10^{14}$ vg/kg, or $2.0\times10^{14}$ vg/kg. In one embodiment, the muscular dystrophy is limb-girdle muscular dystrophy.

In addition, the dose of the rAAV administered is about $1.5\times10^{13}$ vg to about $3.5\times10^{16}$ vg, or $3\times10^{13}$ vg to $1\times10^{16}$ vg, or about $1.5\times10^{13}$ vg to about $2\times10^{15}$ vg, or about $1.5\times10^{13}$ vg to about $1\times10^{15}$ vg. In addition, in any of the methods, the dose of rAAV is administered at a concentration of about 10 mL/kg. In one embodiment, the muscular dystrophy is limb-girdle muscular dystrophy. In one embodiment, the muscular dystrophy is limb-girdle muscular dystrophy, type 2D. The doses in this disclosure, expressed in either vg or vg/kg, are based on a titration qualification method by quantitative PCR (qPCR). The qPCR-based titration method is known in the art.

In addition, provided are methods of treating muscular dystrophy in a subject in need thereof comprising the step of administering a recombinant adeno-associated virus (rAAV) scAAVrh74.tMCK.hSGCA, wherein the rAAV is administered using a systemic route of administration and at a dose of about $1.0\times10^{12}$ vg/kg to about $2.0\times10^{15}$ vg/kg; wherein the level of alpha-sarcoglycan gene expression in a cell of the subject is increased after administration of the rAAV as compared to the level of alpha-sarcoglycan gene expression before administration of the rAAV; wherein the serum CK level in the subject is decreased after administration of the rAAV as compared to serum CK level before administration of the rAAV; and/or wherein the locomotor activity and specific-force generation are increased; wherein fibrosis is reduced; wherein the resistance to contraction-induced injury in tibialis anterior muscle is increased; and/wherein the number of alpha-sarcoglycan positive fibers in the muscle tissue of the subject is increased after administration of the rAAV as compared to the number of alpha-sarcoglycan positive fibers before administration of the rAAV; wherein the fiber diameter size in the muscle tissue of the subject is increased after administration of the rAAV as compared to the number of the fiber diameter before administration of the rAAV; or wherein the central nucleation in the muscle tissue of the subject is reduced after administration of the rAAV as compared to the central nucleation before administration of the rAAV. The muscle tissues include but are not limited to triceps, tibialis anterior, soleus, gastrocnemius, biceps, trapezius, gluteus, psoas major, deltoids, quadriceps, and diaphragm. In one embodiment, the muscle tissues comprise tibialis anterior, gastrocnemius, gluteus, psoas major, and triceps. The expression of alpha-sarcoglycan is determined by methods known to a person with ordinary skill in the art. In one embodiment, the expression is determined by Western blot, immunochemistry in muscle biopsies, and/or by detecting the number of vector genome per microgram of genomic DNA.

In some embodiments, the disclosure includes a method of treating muscular dystrophy in a subject in need thereof comprising the step of administering a recombinant adeno-associated virus (rAAV) scAAVrh74.tMCK.hSGCA, wherein motor function is demonstrably improved in said human subject as compared to motor function of said human subject before administration of the rAAV.

Provided are methods of increasing alpha-sarcoglycan in a patient in need thereof comprising administering to the patient the scAAVrh74.tMCK.hSGCA construct nucleotide sequence of SEQ ID NO: 1.

In any of the methods, uses and compositions of treating muscular dystrophy provided, the subject is 4-15 years of age, has confirmed alpha-sarcoglycan (SGCA) mutation in both alleles, is negative for AAVrh74 antibodies and/or had >40% or normal 100 meter walk test. In any of the methods, uses and compositions of treating muscular dystrophy provided, the subject is a pediatric subject. In some embodiments, the subject is a pediatric subject, such as a subject ranging in age from 1 to 21 years. In some embodiments, the subject is 1 to 10 years of age, or 2 to 12 years of age, 4 to 15 years of age, or 10 to 19 years of age. The subject, in one embodiment, is an adolescent subject, such as a subject ranging in age from 12 to 21 years. In addition, the subject, in one embodiment, is a young adult subject such as a subject ranging in age from 15 to 29 years of age or 18-39 years of age. In some embodiments, the subject is a middle-aged adult or an elderly subject, such that the middle-aged adult may range in age from 25-55 years of age, the older adult subject may range in age over 50 years of age, and the elderly subject may range in age over 65 years of age. In some embodiments, the rAAV is administered by injection, infusion or implantation. For example, the rAAV is administered by infusion over approximately 1 to 2 hours. In addition, the rAAV is administered by an intravenous route through a peripheral limb vein.

In the methods of treating muscular dystrophy in a human subject in need thereof comprising the step of administering a recombinant adeno-associated virus (rAAV) scAAVrh74.tMCK.hSGCA, wherein the rAAV is administered using a systemic route of administration and at a dose of about $1.0\times10^{12}$ vg/kg to about $5.0\times10^{14}$ vg/kg and the rAAV comprises a nucleotide sequence at least 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 1. In another embodiment, the rAAV comprises a nucleotide sequence set forth in SEQ ID NO: 1. In one embodiment, the rAAV encodes a protein comprising a polypeptide sequence that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 2. In another embodiment, the rAAV comprises a nucleotide sequence encoding a protein comprising a polypeptide sequence set forth in SEQ ID NO: 2. In addition, the any of the disclosed rAAV comprise a promoter such as the tMCK promoter sequence of SEQ ID NO: 7 and/or SEQ ID NO:9. In some embodiments, the rAAV is of the serotype AAVrh.74. In on embodiment, the rAAV comprises a 5' inverted terminal repeat sequence of SEQ ID NO: 8. In another embodiment, the rAAV comprises a 3' inverted terminal repeat sequence of SEQ ID NO: 4 and/or 11. In another embodiment, the rAAV comprises a poly A sequence of SEQ ID NO: 5 and/or SEQ ID NO: 10.

AAV dosage can be determined by multiple methods, which include but are not limited to LISA, assessment of the reverse transcriptase activity, FACS, transduction assays northern blotting (e.g., semi-quantitative northern), dot blot analysis or PCR (e.g., qPCR). It is well known that the AAV doses can be determined by measuring AAV vector genomes with quantitative real-time PCR (qPCR). Such qPCR methods overcome the inconsistency or arbitrary results from conventional transduction assays. In one embodiment of PCR dosage determination, plasmid DNA is used as a calibration standard. The forms of the plasmids can impact the dosage results from the qPCR methods. In one embodiment, the circular or supercoiled DNA or plasmids are used as a quantification standard. In another embodiment, the linearized DNA or plasmids are used as the quantification standard.

The term "supercoiled DNA" or "supercoiled plasmid" refers to a DNA or plasmid that comprises no free end. The term "linearized DNA" or "linearized plasmid" refer to a DNA or plasmid that comprises a free 5' end and a free 3' end, which are not linked to each other. In one embodiment, a linearized DNA or plasmid is obtained by a restriction digest of a circular DNA (e.g. plasmid DNA) or by a restriction digest of a dbDNA. In another embodiment, the restriction digest is performed using enzymes that generate at least one blunt end.

In an exemplary embodiment, methods of treating muscular dystrophy in a human subject in need thereof comprise the step of administering a recombinant adeno-associated virus (rAAV) scAAVrh74.tMCK7.hSGCA, wherein the rAAV is administered using a systemic route of administration and at a dose of about $1.0\times10^{12}$ vg/kg to about $5.0\times10^{14}$ vg/kg, wherein the human subject is suffering from limb-girdle muscular dystrophy. In one embodiment, the rAAV is administered by intravenous infusion over approximately 1 to 2 hours at a dose of about $5.0\times10^{13}$ vg/kg, $1.0\times10^{14}$ vg/kg, or $2.0\times10^{14}$ vg/kg based on a supercoiled DNA or plasmid as the quantitation standard, and wherein the rAAV comprises the scAAVrh74. tMCK7.hSGCA construct nucleotide sequence of SEQ ID NO: 1. In another embodiment, the dose is about $1.85\times10^{13}$ vg/kg or $7.41\times10^{13}$ vg/kg based on a linearized DNA or plasmid as the quantitation standard.

The disclosure also provides a method of increasing sarcoglycan expression in muscle tissue of a subject comprising administering to the subject a scAAVrh74.tMCK.hSGCA construct comprising a nucleotide sequence at least 90% identical, at least 95% identical, or 99% identical to SEQ ID NO: 1.

The disclosure further provides a method of improving muscle function of a subject comprising administering to the subject a construct comprising a nucleotide sequence at least 90% identical, at least 95% identical, or 99% identical to SEQ ID NO: 1.

In some aspects, the subject suffers from a genetic mutation in a gene encoding a sarcoglycan protein or a muscular dystrophy. In some aspects, the subject suffers from a genetic mutation in a gene encoding alpha-sarcoglycan protein.

In any of the provided methods, the level of alpha-sarcoglycan gene expression in a cell of the subject is increased after administration of scAAVrh74.tMCK.hSGCA construct as compared to the level of alpha-sarcoglycan gene expression before administration of scAAVrh74.tMCK.hSGCA construct.

In addition, in any of the provided methods, the expression of the alpha-sarcoglycan gene in the cell is detected by measuring the alpha-sarcoglycan protein level on a Western blot or immunohistochemistry in muscle biopsied before and after administration of scAAVrh74.tMCK.hSGCA construct.

In any of the provided methods, the level of alpha-sarcoglycan protein is increased after administration of scAAVrh74.tMCK.hSGCA construct. For example, the level of the level of alpha-sarcoglycan protein is increased by at least 33% as detected by measuring the alpha-sarcoglycan protein level on a Western blot in muscle biopsied before and after administration of scAAVrh74.tMCK.hSGCA construct, or the level of alpha-sarcoglycan protein is measured by immunohistochemistry in muscle biopsies and/or by detecting the number of vector genome per microgram of genomic DNA before and after administration of scAAVrh74.tMCK.hSGCA construct.

In any of the methods provided herein, the serum CK level in the subject is decreased after administration of scAAVrh74.tMCK.hSGCA construct as compared to serum CK level before administration of scAAVrh74.tMCK.hSGCA construct.

In any of the methods provided herein, the number of alpha-sarcoglycan positive fibers in the muscle tissue of the subject is increased after administration of scAAVrh74.tMCK.hSGCA construct as compared to the number of alpha-sarcoglycan positive fibers before administration of scAAVrh74.tMCK.hSGCA construct. For example, the number of alpha-sarcoglycan positive fibers is detected by measuring the alpha-sarcoglycan protein level by Western blot or immunohistochemistry on muscle biopsies before and after administration of scAAVrh74.tMCK.hSGCA construct. For example, the number of alpha-sarcoglycan positive fibers in the muscle tissue of the subject is increased after administration of scAAVrh74.tMCK.hSGCA construct.

In any of the methods provided herein, the level of alpha-sarcoglycan in the subject is increased after administration of the rAAV as compared to the level of alpha-sarcoglycan before administration of scAAVrh74.tMCK.hSGCA construct. The level of alpha-sarcoglycan is detected by measuring the alpha-sarcoglycan protein level by immunohistochemistry or Western blot on muscle biopsies before and after administration of scAAVrh74.tMCK.hSGCA construct.

Another embodiment provides for methods expressing alpha-sarcoglycan gene in a patient cell comprising administering to the patient the scAAVrh74.tMCK.hSGCA construct nucleotide sequence of SEQ ID NO: 1. In any of the provided methods of expressing alpha-sarcoglycan gene in a patient cell, expression of the alpha-sarcoglycan gene in the patient cell is detected by measuring the alpha-sarcoglycan protein level on a Western blot or immunohistochemistry in muscle biopsies before and after administration of the scAAVrh74.tMCK.hSGCA construct. In one embodiment, the alpha-sarcoglycan gene is measured in the patient by detecting greater than one rAAV vector genome copy per nucleus. In another embodiment, the expression of the alpha-sarcoglycan gene is measured in the subject by detecting the number of vector genome per microgram of genomic DNA.

Methods of decreasing serum CK levels in a patient in need thereof, the method comprising administering to the subject the scAAVrh74.tMCK.hSGCA construct nucleotide sequence of SEQ ID NO: 1 are also provided.

Methods of increasing alpha-sarcoglycan positive fibers in a patient muscle tissue comprising administering to the subject the scAAVrh74.tMCK.hSGCA construct nucleotide sequence of SEQ ID NO: 1 are provided. In any of these methods, the number of alpha-sarcoglycan positive fibers is detected by measuring the alpha-sarcoglycan protein level by Western blot or immunohistochemistry on muscle biopsies before and after administration of the rAAV.

Another embodiment provides for methods of increasing the expression of alpha-sarcoglycan in a subject in need thereof comprising administering to the subject the scAAVrh74.tMCK.hSGCA construct nucleotide sequence of SEQ ID NO: 1. In any of these methods, the level of alpha-sarcoglycan is detected by measuring the alpha-sarcoglycan protein level by Western blot or immunohistochemistry on muscle biopsies before and after administration of the rAAV.

A therapeutically effective amount of the rAAV vector is a dose of rAAV ranging from between about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $5\times10^{13}$ vg/kg to about $2\times10^{14}$ vg/kg, or about $2.0\times10^{13}$ vg/kg to about $3.0\times10^{14}$ vg/kg. In another embodiment, the dose is about $5.0\times10^{13}$ vg/kg, about $1.0\times10^{14}$ vg/kg, or about $2.0\times10^{14}$ vg/kg. In another embodiment, the dose is $5.0\times10^{13}$ vg/kg, $1.0\times10^{14}$ vg/kg, or $2.0\times10^{14}$ vg/kg. The invention is also contemplated to include compositions comprising these ranges of rAAV vector.

Dosages may also be expressed in units of viral genomes (vg). The titers of rAAV may be determined by the supercoiled DNA or plasmid quantitation standard or the linearized DNA or plasmid quantitation standard. The titer or dosage of AAV vectors can vary based on the physical forms of plasmid or DNA as a quantitation standard. For example, the value of titer or dosage may vary based off of a supercoiled standard qPCR titering method or a linear standard qPCR titering method. In one embodiment, the dosage in this disclosure is based on a supercoiled DNA or plasmid as the quantitation standard. In another embodiment, the dosage in this disclosure is based on a linearized DNA or plasmid as the quantitation standard. Therefore, in one embodiment, the therapeutically effective amount of the rAAV vector is a dose of rAAV ranging from between about $1.0\times10^{12}$ vg/kg to about $2.0\times10^{15}$ vg/kg, about $5\times10^{12}$ vg/kg to about $1.0\times10^{15}$ vg/kg, about $1.0\times10^{13}$ vg/kg to about $5.0\times10^{14}$ vg/kg, about $5\times10^{13}$ vg/kg to about $2\times10^{14}$ vg/kg, or about $2.0\times10^{13}$ vg/kg to about $3.0\times10^{14}$ vg/kg based on a supercoiled DNA or plasmid as the quantitation standard. In another embodiment, the dose is about $5.0\times10^{13}$ vg/kg, about $1.0\times10^{14}$ vg/kg, or about $2.0\times10^{14}$ vg/kg based on a supercoiled DNA or plasmid as the quantitation standard. In another embodiment, the dose is $5.0\times10^{13}$ vg/kg, $1.0\times10^{14}$ vg/kg, or $2.0\times10^{14}$ vg/kg based on a supercoiled DNA or plasmid as the quantitation standard.

In another embodiment, the therapeutically effective amount of the rAAV vector is a dose of rAAV ranging from between about $1.0\times10^{13}$ vg/kg to about $8.0\times10^{13}$ vg/kg, about $1.5\times10^{13}$ vg/kg to about $8.0\times10^{13}$ vg/kg, about $1.6\times10^{13}$ vg/kg to about $8.0\times10^{13}$ vg/kg, about $1.8\times10^{13}$ vg/kg to about $8.0\times10^{13}$ vg/kg, about $1.2\times10^{13}$ vg/kg to about $7.5\times10^{13}$ vg/kg, about $1.9\times10^{13}$ vg/kg to about $7.5\times10^{13}$ vg/kg, about $1.4\times10^{13}$ vg/kg to about $7.4\times10^{13}$ vg/kg, about $1.9\times10^{13}$ vg/kg to about $7.5\times10^{13}$ vg/kg, or about $1.8\times10^{13}$ vg/kg to about $8.0\times10^{13}$ vg/kg based on a linearized DNA or plasmid as the quantitation standard. For example, the therapeutically effective amount of the rAAV vector is a dose of about $1.85\times10^{13}$ vg/kg or $7.41\times10^{13}$ vg/kg based on a linearized DNA or plasmid as the quantitation standard.

In one embodiment, the dose of $5.0\times10^{13}$ vg/kg based on a supercoiled DNA or plasmid as the quantitation standard is equivalent to the dose of $1.85\times10^{13}$ vg/kg based on a linearized DNA or plasmid as the quantitation standard. In another embodiment, the dose of $2.0\times10^{14}$ vg/kg based on a supercoiled DNA or plasmid is equivalent to $7.41\times10^{13}$ vg/kg based on a linearized DNA or plasmid as the quantitation standard. Therefore, in another embodiment, about $1.85\times10^{13}$ vg/kg or $7.41\times10^{13}$ vg/kg based on a linearized DNA or plasmid as the quantitation standard.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the alpha-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein.

A therapeutically effective amount of the rAAV vector is a dose of rAAV ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, or 9e14 vg/kg. The invention also comprises compositions comprising these ranges of rAAV vector.

For example, a therapeutically effective amount of rAAV vector is a dose of 1e13 vg/kg, about 2e13 vg/kg, about 3e13 vg/kg, about 4e13 vg/kg, about 5e13 vg/kg, about 6e13 vg/kg, about 7e13 vg/kg, about 7.4e13 vg/kg, about 8e13 vg/kg, about 9e13 vg/kg, about 1e14 vg/kg, about 2e14 vg/kg, about 3e14 vg/kg, about 4e14 vg/kg and 5e14 vg/kg. The titer or dosage of AAV vectors can vary based on the physical forms of plasmid DNA as a quantitation standard. For example, the value of titer or dosage may vary based off of a supercoiled standard qPCR titering method or a linear standard qPCR tittering method. In one embodiment, a therapeutically effective amount of rAAV is a dose of 5e13 vg/kg based on a supercoiled plasmid as the quantitation standard or a dose of 1.85e13 vg/kg based on a linearized plasmid as the quantitation standard. In another embodiment, a therapeutically effective amount of rAAV is a dose of 2e14 vg/kg based on the supercoiled plasmid as the quantitation standard or a dose of 7.41e13 vg/kg based on the linearized plasmid as the quantitation standard. In another embodiment, the therapeutically effective amount of scAAVrh74.tMCK.hSGCA is a dose ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg. 6e14 vg/kg, 7e14 vg/kg, 8e14 vg/kg, or 9e14 vg/kg, based on the supercoiled plasmid as the quantitation standard. The invention also comprises compositions comprising these doses of rAAV vector.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the β-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein.

Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling. Thus, in another aspect, the application is directed to a formulation that comprises an rAAV that comprises an AAVrh74 derived capsid, a buffer agent, an ionic strength agent, and a surfactant. In one embodiment, the rAAV is at a concentration of about $1.0\times10^{12}$ vg/ml to about $5.0\times10^{14}$ vg/ml. In another embodiment, the rAAV is at a concentration of about $5.0\times10^{12}$ vg/ml to about $1.0\times10^{14}$ vg/ml based on a supercoiled plasmid as the quantitation standard. In another embodiment, the rAAV is at a concentration of about $2.0\times10^{13}$ vg/ml based on a supercoiled plasmid as the quantitation standard. In one embodiment, the rAAV is an scAAVrh74.tMCK.hSGCA vector. In one embodiment, the concentration of rAAV in the composition or formulation is from $1\times10^{13}$ vg/ml to $2\times10^{14}$ vg/ml based on a supercoiled plasmid as the quantitation standard. In another embodiment, the concentration is $2\times10^{13}$ vg/ml, $4\times10^{13}$ vg/ml, or $5\times10^{13}$ vg/ml based on a supercoiled plasmid as the quantitation standard. In one embodiment, the buffer agent comprises one or more of tris, tricine, Bis-tricine, HEPES, MOPS, TES, TAPS, PIPES, and CAPS. In another embodiment, the buffer agent comprises tris with pH 8.0 at concentration of about 5 mM to about 40 mM. In one embodiment, the buffer agent comprises tris with pH 8.0 at about 20 mM. In one embodiment, the ionic strength agent comprises one of more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. In one embodiment, the ionic strength agent comprises $MgCl_2$ at a concentration of about 0.2 mM to about 4 mM. In another embodiment, the ionic strength agent comprises NaCl at a concentration of about 50 mM to about 500 mM. In another embodiment, the ionic strength agent comprises $MgCl_2$ at a concentration of about 0.2 mM to about 4 mM and NaCl at a concentration of about 50 mM to about 500 mM. In another embodiment, the ionic strength agent comprises $MgCl_2$ at a concentration of about 1 mM and NaCl at a concentration of about 200 mM. In one embodiment, the surfactant comprises one or more of a sulfonate, a sulfate, a phosphonate, a phosphate, a Poloxamer, and a cationic surfactant. In one embodiment, the Poloxamer comprises one or more of Poloxamer 124, Poloxamer 181, Poloxamer 184, Poloxamer 188, Poloxamer 237, Poloxamer 331, Poloxamer 338, and Poloxamer 407. In one embodiment, the surfactant comprises the Poloxamer at a concentration of about 0.00001% to about 1%. In another embodiment, the surfactant comprises Poloxamer 188 at a concentration of about 0.001%. For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

Thus, also described herein are methods of administering an effective dose (or doses, administered essentially simultaneously or doses given at intervals) of rAAV that encode alpha-sarcoglycan to a mammalian subject in need thereof.

All publications and patents mentioned herein are hereby incorporated by reference in their entirety as if each individual publication or patent was specifically and individually indicated to be incorporated by reference. In case of conflict, the present application, including any definitions herein, will control.

The invention is further described in the following Examples, which do not limit the scope of the invention described in the claims.

EXAMPLES

Preclinical studies using AAVrh74.tMCK.hSCGA are described in International Patent Publication No. WO 2013/078316 and U.S. Pat. Nos. 9,434,928 and 10,105,453, which are incorporated by reference herein in its entirety.

Example 1 scAAVrh74.tMCK.hSGCA Construction

The scAAVrh74.tMCK.hSGCA transgene cassette was made using an adeno-associated virus (AAV) vector DNA plasmid pAAV.tMCK.aSG-neo, by inserting the tMCK expression cassette driving a codon-optimized human alpha-SG cDNA sequence (human cDNA, Genbank Accession #U08895) into the self-complementary vector backbone pHpa7. The only viral sequences included in this vector are the inverted terminal repeats of AAV2, which are required for both viral DNA replication and packaging of the rAAV vector genome. One of the inverted terminal repeats (ITRs) has a targeted deletion of the terminal resolution site (TRS) to restrict replication from this ITR facilitating generation of the dimeric replicative form for self-complementary vector packaging. The AAVrh74 virus has been proven in mice, non-human primates (NHPs), and humans to be safe and highly efficient in transducing muscle across the vascular barrier.

The recombinant AAV, (sc)rAAVrh74.tMCK.hSGCA, was made in by triple transfection. A qPCR-based titration method was used to determine an encapsulated vg titer utilizing a Prism 7500 Fast Taqman detector system (PE Applied Biosystems). The construct comprises a chimeric intron to promote high-level expression. The chimeric intron is composed of the 5' donor site from the first intron of the human β-globin gene and the branchpoint and 3' splice acceptor site from the intron that is between the leader and the body of an immunoglobulin gene heavy chain variable region. The rAAV also comprises a synthetic SV40 polyadenylation signal is used for efficient transcription termination. A schematic of the expression cassette is shown below in FIG. 1. The vector was produced using the human alpha-sacroglycan (alpha-SG) gene flanked by AAV2 ITR sequences and encapsidated into AAVrh74 virions. The construct contains the tMCK immediate early promoter/enhancer (GenBank Accession No. M21390) and uses the ß-globin intron for high-level expression.

A single strand AAV vector (ssAAV), once in the nucleus, requires cell-mediated synthesis of the second strand before it is ready for replication and transcription. An exemplary self-complementary AAV vector (scAAV) has the structure as set out in FIG. 1 and the annoted nucleotide sequence provided in FIG. 2 and is described in Table below. This scAAV is superior to ssAAV in gene therapy because the scAAV bypasses the rate-limiting step of the cellular synthesis of the second-strand as required in a ssAAV.

Table 1

Molecular Features of scAAVrh.74.tMCK.hSGCA

| TYPE | START | END | NAME | DESCRIPTION |
|---|---|---|---|---|
| REGION | 1 | 130 | 3' ITR | Self-complementary sequence 3' inverted terminal repeat |
| REGION | 203 | 255 | PolyA | Self-complementary sequence polyA |
| GENE | 256 | 1419 | hSCGA cDNA | Self-complementary hSCGA cDNA |
| REGION | 1623 | 2336 | tMCK | Self-complementary tMCK promoter sequence |
| REGION | 2367 | 2491 | 5' ITR | 5' ITR |
| GENE | 2522 | 3235 | tMCK | tMCK promoter sequence |
| GENE | 3439 | 4602 | hSCGB cDNA | hSCGB cDNA |
| REGION | 4603 | 4655 | PolyA | PolyA |
| REGION | 4728 | 4857 | 3' ITR | 3' ITR |

What is claimed is:

1. A polynucleotide sequence comprising the nucleotide sequence at least 95% identical to the nucleotide sequence of SEQ ID NO: 1.

2. The polynucleotide sequence of claim 1, wherein the nucleotide sequence comprises the nucleotide sequence or SEQ ID NO: 1.

3. A recombinant AAV (rAAV) comprising the polynucleotide sequence of claim 1.

4. The recombinant AAV of claim 3, wherein the vector is of the serotype AAV1, AAV2, AAV4, AAV5, AAV6, AAV7, AAV8, AAV9, AAV10, AAV11, AAV12, AAV13, AAV rh.74, or a variant thereof.

5. A composition comprising the recombinant AAV of claim 3.

6. A method of treating muscular dystrophy of alpha-sarcoglycanopathy in a subject in need thereof comprising administering to the subject the recombinant AAV of claim 3.

7. A method of increasing muscular force and/or muscle mass in a subject suffering from muscular dystrophy comprising administering to the subject the recombinant AAV of claim 3.

8. A method of reducing fibrosis in a subject suffering from muscular dystrophy comprising administering to the subject the recombinant AAV of claim 3.

9. A method of reducing contraction-induced injury in a subject suffering from muscular dystrophy comprising administering to the subject the recombinant AAV of claim 3.

10. A method of increasing alpha-sarcoglycan positive fibers and/or decreasing CK level in a subject's muscle tissue comprising administering to the subject the recombinant AAV of claim 3.

11. The method of claim 6, wherein the subject is suffering from limb-girdle muscular dystrophy.

12. The method of claim 6, wherein the recombinant AAV or the composition is administered systemically.

13. The method of claim 6, wherein the rAAV is administered at a dose about i) $5\times10^{13}$ vg/kg to about $2\times10^{14}$ vg/kg based on a supercoiled DNA or plasmid as the quantitation standard, ii) about $5\times10^{13}$ vg/kg based on a supercoiled DNA or plasmid as the quantitation standard, iii) about $1\times10^{14}$ vg/kg based on a supercoiled DNA or plasmid as the quantitation standard, iv) $2\times10^{14}$ vg/kg based on a supercoiled DNA or plasmid as the quantitation standard, v) about $1.85\times10^{13}$ vg/kg based on a linearized DNA or plasmid as the quantitation standard or vi) $7.41\times10^{13}$ vg/kg based on a linearized DNA or plasmid as the quantitation standard.

14. A host cell comprising the polynucleotide of claim 1.

15. The cell of claim 14, wherein the cell is a eukaryotic cell, a bacterial cell, an insect cell, or a yeast cell.

16. The cell of claim 14, wherein the cell is a 293 cell, a Hela cell, MRC-5 cell, WI-38 cell, Vero cell or FrhL-2 cell.

17. A method of producing a recombinant AAV (rAAV) particle comprising culturing a host cell of claim 14.

18. The polynucleotide sequence of claim 1, wherein the 95% percentage identity is determined by BLAST as an alignment tool, with a default parameters::genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

* * * * *

SEQUENCE LISTING

```
Sequence total quantity: 11
SEQ ID NO: 1              moltype = DNA  length = 4857
FEATURE                   Location/Qualifiers
misc_feature              1..4857
                          note = scAAV construct sequence
source                    1..4857
                          mol_type = other DNA
                          organism = synthetic construct
SEQUENCE: 1
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
agaggcgcgc ccctgcagga cacacaaaaa accaacacac agatctaatg aaaataaaga  240
tcttttattg cggcctcaat gctggtccag aatcagtggc acctgggcgc tatccactct  300
agggggcagc cgttcgccag tgtgcacatt aaacataggc agtgtactca gtggccttgg  360
cacctcccta gaagcagcca tctggcgcag ttcctcggtg ttgccgtgaa tagtacaatg  420
gtgcaccatc tggatatcag atgtggccag gtctctcttc agccgtccct ctctccgaca  480
gcacatcaca taagccagca gcagggtcag cagcagagcc accagcagag gcaccagcag  540
agtcaccaga gcgtccacca ggaaatccct gtctggggct tctgttggag gacaaaagaa  600
aggatcgtgc tccaggattc cgtctccagg ggttggcact tcgtcagctg gctcaggcac  660
agatttatcc accagagtca cgttgcacca gtccacgcga aaatgggggg ccagtgtgtc  720
ataacaggac agcagtggtg gctgtccctg agcgcaccta gcgtgactat caggagaagc  780
caccatcttc aggcaggtgg agaatgggga agcgcttccc actttaatgt acaccccttc  840
cttccttccc tcgattggca gtggcaccct tcctccccta tccagagcgc tagtcacatt  900
cagcagctgc agttctcctg gctcccacag tcctcccaga gcggacagaa atctgctggc  960
gggtgttgat ggcagcactt cctcagcgtc gtgtgaccgc accaggaact cggcctgata  1020
aggcagcagg ggtccttctg gatccccaat ctccagcacc aggcgctgcc tggtagtatc  1080
aaaactgtcg cggttgtaag ctgtcacttc gatcacctgc agtcccctgt cctctggggt  1140
agcgcttcca tacaggaatc caggatggtg gggtgatctc tgggtgtatc tcagccaccg  1200
tggcagatca ggatggccct gcagatgggc gtggtaagtg atatgcacag caggtggcac  1260
agccacgtgt tctggcagac tcagaaatgt ctcatggtcc agggtgtgca cgaacacccg  1320
gcccaccagt gggtgcagtg tggtctgctg agcctcggta tctcccagtc cagccagcag  1380
caccaccagc agaggagtcc agaacagtgt ctcggccatg gtggtaccac gcgctgtaat  1440
tgaactggga gtggacacct gtggagagaa aggcaaagtg gatgtcagta agaccaatag  1500
gtgcctatca gaaacgcaag agtcttctct gtctcgacaa gcccagtttc tattggtctc  1560
cttaaacctg tcttgtaacc ttgatactta cctgcccagt gcctcacgac caacttctgc  1620
aggtgacccg gggcagccc ctgtgcccct gggttatata gaggagccta cagggtgtga  1680
ctagccagga ggggctgtcc ccagggagga ccagggacag ggttattttt agagcgagct  1740
tctcctccat ggtgtacaga gcctaagacc caggcaccgg ggtggggtaa ccgctcaggc  1800
tcaggcagca ggtgttgggg gggggggca gcaggtgttg gggttaatta taaccaggca  1860
tctcgggtgt ccccaggcct tgcctcctta catgggcagc ctagacccgt agtggtccac  1920
cagggacagg gttattttta gagcgagctt ctcctccatg gtgtacagag cctaagaccc  1980
aggcaccggg gtggggtaac cgctcaggct caggcagcag gtgttggggg gggggggca  2040
gcaggtgttg gggttaatta taaccaggca tctcgggtgt ccccaggcct tgcctcctta  2100
catgggcagc atagacccgt agtggatcca ccagggacag ggttattttt agagcgagct  2160
tctcctccat ggtgtacaga gcctaagacc caggcaccgg ggtggggtaa ccgctcaggc  2220
tcaggcagca ggtgttgggg ggggggggc agcaggtgtt ggggttaatt ataaccaggc  2280
atctcgggtg tccccaggcc ttgcctcctt acatgggcag cctagacccg tagtggggca  2340
tgcaagtttg cggccgccaa ttggttaacc ccactccctc tctgcgcgct cgctcgctca  2400
ctgaggccgc ccgggcaaag cccgggcgtc gggcgacctt tggtcgcccg gcctcagtga  2460
gcgagcgagc gcgcagagag ggagtggggt taaccaattg gcggccgcaa acttgcatgc  2520
cccactacgg gtctaggctg cccatgtaag gaggcaaggc ctggggacac ccgagatgcc  2580
tggttataat taaccccaac acctgctgcc cccccccccc caacacctgc tgcctgagcc  2640
tgagcggtta ccccaccccg gtgcctgggt cttaggctct gtacaccatg gaggagaagc  2700
tcgctctaaa aataaccctg tccctggtgg atccactacg ggtctatgct gcccatgtaa  2760
ggaggcaagg cctggggaca cccgagatgc ctggttataa ttaaccccaa cacctgctgc  2820
cccccccccc ccaacacctg ctgcctgagc ctgagcggtt accccacccc ggtgcctggg  2880
tcttaggctc tgtacaccat ggaggagaag ctcgctctaa aaataaccct gtccctggtg  2940
gaccactacg ggtctaggct gcccatgtaa ggaggcaagg cctggggaca cccgagatgc  3000
ctggttataa ttaaccccaa cacctgctgc cccccccccc caacacctgc tgcctgagcc  3060
```

```
tgagcggtta ccccaccccg gtgcctgggt cttaggctct gtacaccatg gaggagaagc  3120
tcgctctaaa aataaccctg tccctggtcc tccctgggga cagcccctcc tggctagtca  3180
caccctgtag gctcctctat ataacccagg ggcacagggg ctgcccccgg gtcacctgca  3240
gaagttggtc gtgaggcact gggcaggtaa gtatcaaggt tacaagacag gtttaaggag  3300
accaatagaa actgggcttg tcgagacaga gaagactctt gcgtttctga taggcaccta  3360
ttggtcttac tgacatccac tttgcctttc tctccacagg tgtccactcc cagttcaatt  3420
acagcgcgtg gtaccaccat ggccgagaca ctgttctgga ctcctctgct ggtggtgctg  3480
ctggctggac tgggagatac cgaggctcag cagaccacac tgcacccact ggtgggccgg  3540
gtgttcgtgc acaccctgga ccatgagaca tttctgagtc tgccagaaca cgtggctgtg  3600
ccacctgctg tgcatatcac ttaccacgcc catctgcagg gccatcctga tctgccacgg  3660
tggctgagat acacccagag atcaccccac catcctggat tcctgtatgg aagcgctacc  3720
ccagaggaca ggggactgca ggtgatcgaa gtgacagctt acaaccgcga cagttttgat  3780
actaccaggc agcgcctggt gctggagatt ggggatccag aaggacccct gctgccttat  3840
caggccgagt tcctggtgcg gtcacacgac gctgaggaag tgctgccatc aacacccgcc  3900
agcagatttc tgtccgctct gggaggactg tgggagccag gagaactgca gctgctgaat  3960
gtgactagcg ctctggatag gggaggaagg gtgccactgc caatcgaggg aaggaaggaa  4020
ggggtgtaca ttaaagtggg aagcgcttcc ccattctcca cctgcctgaa gatggtggct  4080
tctcctgata gtcacgctag gtgcgctcag ggacagccac cactgctgtc ctgttatgac  4140
acactggccc cccatttttcg cgtggactgg tgcaacgtga ctctggtgga taaatctgtg  4200
cctgagccag ctgacgaagt gccaacccct ggagacggaa tcctggagca cgatcctttc  4260
ttttgtcctc caacagaagc cccagacagg gatttcctgg tggacgctct ggtgactctg  4320
ctggtgcctc tgctggtggc tctgctgctg accctgctgc tggcttatgt gatgtgctgt  4380
cggagagagg gacggctgaa gagagacctg gccacatctg atatccagat ggtgcaccat  4440
tgtactattc acggcaacac cgaggaactg cgccagatgg ctgcttctag ggaggtgcca  4500
aggccactga gtacactgcc tatgtttaat gtgcacactg gcgaacggct gccccctaga  4560
gtggatagcg cccaggtgcc actgattctg gaccagcatt gaggccgcaa taaaagatct  4620
ttattttcat tagatctgtg tgttggtttt ttgtgtgtcc tgcaggggcg cgcctctaga  4680
gcatggctac gtagataagt agcatggcgg gttaatcatt aactacaagg aacccctagt  4740
gatggagttg gccactccct ctctgcgcgc tcgctcgctc actgaggccg ggcgaccaaa  4800
ggtcgcccga cgcccgggct ttgcccgggc ggcctcagtg agcgagcgag cgcgcag     4857
```

```
SEQ ID NO: 2            moltype = DNA  length = 1164
FEATURE                 Location/Qualifiers
misc_feature            1..1164
                        note = hSGCA polynucleotide
source                  1..1164
                        mol_type = other DNA
                        organism = synthetic construct
SEQUENCE: 2
atggccgaga cactgttctg gactcctctg ctggtggtgc tgctggctgg actgggagat  60
accgaggctc agcagaccac actgcaccca ctggtgggcc gggtgttcgt gcacaccctg  120
gaccatgaga catttctgag tctgccagaa cacgtggctg tgccacctgc tgtgcatatc  180
acttaccacg cccatctgca gggccatcct gatctgccac ggtggctgag atacacccag  240
agatcacccc accatcctgg attcctgtat ggaagcgcta ccccagagga caggggactg  300
caggtgatcg aagtgacagc ttacaaccgc gacagttttg atactaccag gcagcgcctg  360
gtgctggaga ttggggatcc agaaggaccc ctgctgcctt atcaggccga gttcctggtg  420
cggtcacacg acgctgagga agtgctgcca tcaacacccg ccagcagatt tctgtccgct  480
ctgggaggac tgtgggagcc aggagaactg cagctgctga atgtgactag cgctctggat  540
aggggaggaa gggtgccact gccaatcgag ggaaggaagg aaggggtgta cattaaagtg  600
ggaagcgctt ccccattctc cacctgcctg aagatggtgg cttctcctga tagtcacgct  660
aggtgcgctc agggacagcc accactgctg tcctgttatg acacactggc cccccatttt  720
cgcgtggact ggtgcaacgt gactctggtg gataaatctg tgcctgagcc agctgacgaa  780
gtgccaaccc ctggagacgg aatcctggag cacgatcctt tcttttgtcc tccaacagaa  840
gccccagaca gggatttcct ggtggacgct ctggtgactc tgctggtgcc tctgctggtg  900
gctctgctgc tgaccctgct gctggcttat gtgatgtgct gtcggagaga gggacggctg  960
aagagagacc tggccacatc tgatatccag atggtgcacc attgtactat tcacggcaac  1020
accgaggaac tgcgccagat ggctgcttct agggaggtgc caaggccact gagtacactg  1080
cctatgttta atgtgcacac tggcgaacgg ctgcccccta gagtggatag cgcccaggtg  1140
ccactgattc tggaccagca ttga                                         1164
```

```
SEQ ID NO: 3            moltype = AA  length = 387
FEATURE                 Location/Qualifiers
REGION                  1..387
                        note = hSGCA polypeptide
source                  1..387
                        mol_type = protein
                        organism = synthetic construct
SEQUENCE: 3
MAETLFWTPL LVVLLAGLGD TEAQQTTLHP LVGRVFVHTL DHETFLSLPE HVAVPPAVHI  60
TYHAHLQGHP DLPRWLRYTQ RSPHHPGFLY GSATPEDRGL QVIEVTAYNR DSFDTTRQRL  120
VLEIGDPEGP LLPYQAEFLV RSHDAEEVLP STPASRFLSA LGGLWEPGEL QLLNVTSALD  180
RGGRVPLPIE GRKEGVYIKV GSASPFSTCL KMVASPDSHA RCAQGQPPLL SCYDTLAPHF  240
RVDWCNVTLV DKSVPEPADE VPTPGDGILE HDPFFCPPTE APDRDFLVDA LVTLLVPLLV  300
ALLLTLLLAY VMCCRREGRL KRDLATSDIQ MVHHCTIHGN TEELRQMAAS REVPRPLSTL  360
PMFNVHTGER LPPRVDSAQV PLILDQH                                      387
```

```
SEQ ID NO: 4            moltype = DNA  length = 130
FEATURE                 Location/Qualifiers
misc_feature            1..130
```

```
                         note = complement of 3' ITR
source                   1..130
                         mol_type = other DNA
                         organism = synthetic construct
SEQUENCE: 4
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 5             moltype = DNA  length = 53
FEATURE                  Location/Qualifiers
misc_feature             1..53
                         note = complement of polyA
source                   1..53
                         mol_type = other DNA
                         organism = synthetic construct
SEQUENCE: 5
cacaaaaaac caacacacag atctaatgaa aataaagatc ttttattgcg gcc         53

SEQ ID NO: 6             moltype = DNA  length = 1164
FEATURE                  Location/Qualifiers
misc_feature             1..1164
                         note = complement of SGCA DNA (SGCA Codon Optimized)
source                   1..1164
                         mol_type = other DNA
                         organism = synthetic construct
SEQUENCE: 6
tcaatgctgg tccagaatca gtggcacctg ggcgctatcc actctagggg gcagccgttc  60
gccagtgtgc acattaaaca taggcagtgt actcagtggc cttggcacct ccctagaagc  120
agccatctgg cgcagttcct cggtgttgcc gtgaatagta caatggtgca ccatctggat  180
atcagatgtg gccaggtctc tcttcagccg tccctctctc cgacagcaca tcacataagc  240
cagcagcagg gtcagcagca gagccaccag cagaggcacc agcagagtca ccagagcgtc  300
caccaggaaa tccctgtctg gggcttctgt tggaggacaa aagaaaggat cgtgctccag  360
gattccgtct ccaggggttg gcacttcgtc agctggctca ggcacagatt tatccaccag  420
agtcacgttg caccagtcca cgcgaaaatg gggggccagt gtgtcataac aggacagcag  480
tggtggctgt ccctgagcgc acctagcgtg actatcagga gaagccacca tcttcaggca  540
ggtggagaat ggggaagcgc ttcccacttt aatgtacacc ccttccttcc ttccctcgat  600
tggcagtggc acccttcctc ccctatccag agcgctagtc acattcagca gctgcagttc  660
tcctggctcc cacagtcctc ccagagcgga cagaaatctg ctggcgggtg ttgatggcag  720
cacttcctca gcgtcgtgtg accgcaccag gaactcggcc tgataaggca gcaggggtcc  780
ttctggatcc ccaatctcca gcaccaggcg ctgcctggta gtatcaaaac tgtcgcggtt  840
gtaagctgtc acttcgatca cctgcagtcc cctgtcctct ggggtagcgc ttccatacag  900
gaatccagga tggtggggtg atctctgggt gtatctcagc caccgtggca gatcaggatg  960
gccctgcaga tgggcgtggt aagtgatatg cacagcaggt ggcacagcca cgtgttctgg  1020
cagactcaga aatgtctcat ggtccagggt gtgcacgaac acccggccca ccagtgggtg  1080
cagtgtggtc tgctgagcct cggtatctcc cagtccagcc agcagcacca ccagcagagg  1140
agtccagaac agtgtctcgg ccat                                         1164

SEQ ID NO: 7             moltype = DNA  length = 714
FEATURE                  Location/Qualifiers
misc_feature             1..714
                         note = complement of tMCK promoter
source                   1..714
                         mol_type = other DNA
                         organism = synthetic construct
SEQUENCE: 7
gtgacccggg ggcagcccct gtgcccctgg gttatataga ggagcctaca gggtgtgact  60
agccaggagg ggctgtcccc agggaggacc agggacaggg ttattttttag agcgagcttc  120
tcctccatgg tgtacagagc ctaagaccca ggcaccgggg tggggtaacc gctcaggctc  180
aggcagcagg tgttgggggg gggggcagc aggtgttggg gttaattata accaggcatc  240
tcgggtgtcc ccaggccttg cctccttaca tgggcagcct agacccgtag tggtccacca  300
gggacagggt tatttttaga gcgagcttct cctccatggt gtacagagcc taagacccag  360
gcaccggggt ggggtaaccg ctcaggctca ggcagcaggt gttggggggg gggggcagc  420
aggtgttggg gttaattata accaggcatc tcgggtgtcc ccaggccttg cctccttaca  480
tgggcagcat agacccgtag tggatccacc agggacaggg ttattttttag agcgagcttc  540
tcctccatgg tgtacagagc ctaagaccca ggcaccgggg tggggtaacc gctcaggctc  600
aggcagcagg tgttgggggg ggggggcag caggtgttgg ggttaattat aaccaggcat  660
ctcgggtgtc cccaggcctt gcctccttac atgggcagcc tagacccgta gtgg        714

SEQ ID NO: 8             moltype = DNA  length = 125
FEATURE                  Location/Qualifiers
misc_feature             1..125
                         note = complement of 5' ITR
source                   1..125
                         mol_type = other DNA
                         organism = synthetic construct
SEQUENCE: 8
aaccccactc cctctctgcg cgctcgctcg ctcactgagg ccgcccgggc aaagcccggg  60
cgtcgggcga cctttggtcg cccggcctca gtgagcgagc gagcgcgcag agagggagtg  120
```

-continued

```
gggtt                                                             125

SEQ ID NO: 9            moltype = DNA  length = 714
FEATURE                 Location/Qualifiers
misc_feature            1..714
                        note = tMCK promoter sequence
source                  1..714
                        mol_type = other DNA
                        organism = synthetic construct
SEQUENCE: 9
ccactacggg tctaggctgc ccatgtaagg aggcaaggcc tggggacacc cgagatgcct  60
ggttataatt aaccccaaca cctgctgccc cccccccccc aacacctgct gcctgagcct  120
gagcggttac ccccaccccgg tgcctgggtc ttaggctctg tacaccatgg aggagaagct  180
cgctctaaaa ataaccctgt ccctggtgga tccactacgg gtctatgctg cccatgtaag  240
gaggcaaggc ctggggacac ccgagatgcc tggttataat taaccccaac acctgctgcc  300
cccccccccc caacacctgc tgcctgagcc tgagcggtta ccccaccccg gtgcctgggt  360
cttaggctct gtacaccatg gaggagaagc tcgctctaaa aataaccctg tccctggtgg  420
accactacgg gtctaggctg cccatgtaag gaggcaaggc ctggggacac ccgagatgcc  480
tggttataat taaccccaac acctgctgcc cccccccccc aacacctgct gcctgagcct  540
gagcggttac cccaccccgg tgcctgggtc ttaggctctg tacaccatgg aggagaagct  600
cgctctaaaa ataaccctgt ccctggtcct ccctggggac agcccctcct ggctagtcac  660
accctgtagg ctcctctata taacccaggg gcacaggggc tgcccccggg tcac        714

SEQ ID NO: 10           moltype = DNA  length = 53
FEATURE                 Location/Qualifiers
misc_feature            1..53
                        note = poly A
source                  1..53
                        mol_type = other DNA
                        organism = synthetic construct
SEQUENCE: 10
ggccgcaata aaagatcttt attttcatta gatctgtgtg ttggtttttt gtg         53

SEQ ID NO: 11           moltype = DNA  length = 130
FEATURE                 Location/Qualifiers
misc_feature            1..130
                        note = 3' ITR
source                  1..130
                        mol_type = other DNA
                        organism = synthetic construct
SEQUENCE: 11
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                         130
```